United States Patent
Mayer et al.

(10) Patent No.: US 10,542,972 B2
(45) Date of Patent: Jan. 28, 2020

(54) JOINING ELEMENT

(71) Applicant: DePuy Synthes Products, Inc., Raynham, MA (US)

(72) Inventors: Joerg Mayer, Oberdorf (CH); Jochen Ganz, Oberdorf (CH); Beat Keller, Oberdorf (CH); Ralph Hertel, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 150 days.

(21) Appl. No.: 15/687,784

(22) Filed: Aug. 28, 2017

(65) Prior Publication Data

US 2017/0354411 A1 Dec. 14, 2017

Related U.S. Application Data

(60) Continuation of application No. 13/800,889, filed on Mar. 13, 2013, now Pat. No. 9,757,121, which is a (Continued)

(30) Foreign Application Priority Data

May 4, 2005 (CH) .................. SE0834/05

(51) Int. Cl.
*A61B 17/04* (2006.01)
*A61L 17/00* (2006.01)
*A61B 17/06* (2006.01)
*B29C 61/06* (2006.01)

(52) U.S. Cl.
CPC ........ *A61B 17/06166* (2013.01); *A61B 17/04* (2013.01); *A61L 17/00* (2013.01); *B29C 61/0608* (2013.01)

(58) Field of Classification Search
CPC .............. A61B 17/06166; A61B 17/04; A61B 2017/06185; A61L 17/00
See application file for complete search history.

(56) References Cited

U.S. PATENT DOCUMENTS 3,847,156 A  11/1974  Trumble
3,942,532 A   3/1976  Hunter et al.
(Continued)

FOREIGN PATENT DOCUMENTS

CN       1623016     6/2005
CN    201543004 U    8/2010
(Continued)

OTHER PUBLICATIONS

Written Opinion of the International Searching Authority for International Application No. PCT/US2013/027943, dated May 14, 2013, 6 pages.

(Continued)

*Primary Examiner* — Melanie R Tyson
(74) *Attorney, Agent, or Firm* — BakerHostetler

(57) ABSTRACT

Disclosed is a joining element (10), especially a suture material for surgical use. The joining element (10) is composed of a first material (12) that is essentially rigid during impingement by a relatively short-lasting tensile load on opposite sides as well as a second material (11) which is connected to the first material. The second material is substantially rigid during impingement by said tensile load on opposite sides while contracting slowly during a second period of time that is longer than the first period of time.

10 Claims, 12 Drawing Sheets

Related U.S. Application Data division of application No. 11/913,656, filed as application No. PCT/EP2006/062061 on May 4, 2006, now Pat. No. 8,870,915.

(56) References Cited

U.S. PATENT DOCUMENTS

| | | |
|---|---|---|
| 4,209,859 A | 7/1980 | Hoffman |
| 4,461,298 A | 7/1984 | Shalaby et al. |
| 4,621,638 A | 11/1986 | Silvestrini |
| 4,662,886 A | 5/1987 | Moorse et al. |
| 4,857,602 A | 8/1989 | Casey et al. |
| 4,946,467 A | 8/1990 | Ohi et al. |
| 4,959,069 A | 9/1990 | Brennan et al. |
| 4,990,158 A | 2/1991 | Kaplan et al. |
| 5,102,420 A | 4/1992 | Hunter et al. |
| 5,133,738 A | 7/1992 | Korthoff et al. |
| 5,147,400 A | 9/1992 | Kaplan et al. |
| 5,217,495 A | 6/1993 | Kaplan et al. |
| 5,234,006 A | 8/1993 | Eaton et al. |
| 5,314,446 A | 5/1994 | Hunter et al. |
| 5,464,424 A | 11/1995 | O'Donnell, Jr. |
| 5,562,736 A | 10/1996 | Ray et al. |
| 5,651,377 A | 7/1997 | O'Donnell, Jr. |
| 5,810,851 A | 9/1998 | Yoon |
| 5,952,232 A | 9/1999 | Rothman |
| 6,022,376 A | 2/2000 | Assell et al. |
| 6,045,571 A | 4/2000 | Hill et al. |
| 6,090,117 A | 7/2000 | Shimizu |
| 6,174,333 B1 | 1/2001 | Kadiyala et al. |
| 6,197,043 B1 | 3/2001 | Davidson |
| 6,251,137 B1 | 6/2001 | Andrews et al. |
| 6,296,659 B1 | 10/2001 | Foerster |
| 6,605,294 B2 | 8/2003 | Sawhney |
| 7,033,603 B2 | 4/2006 | Nelson et al. |
| 7,175,632 B2 | 2/2007 | Singhatat et al. |
| 7,270,666 B2 | 9/2007 | Lombardo et al. |
| 7,285,124 B2 | 10/2007 | Foerster |
| 7,329,271 B2 | 2/2008 | Koyfman et al. |
| 7,338,492 B2 | 3/2008 | Singhatat et al. |
| 7,431,725 B2 | 10/2008 | Stack et al. |
| 7,469,526 B2 | 12/2008 | Patrick et al. |
| 7,674,271 B2 | 3/2010 | Bjerken |
| 7,678,138 B2 | 3/2010 | Fitts et al. |
| 7,762,287 B2 | 7/2010 | Liao |
| 7,829,485 B2 | 11/2010 | Mikura |
| 7,955,539 B2 | 6/2011 | Patel et al. |
| 8,118,834 B1 | 2/2012 | Goraltchouk et al. |
| 8,870,915 B2 | 10/2014 | Mayer et al. |
| 2002/0029066 A1 | 3/2002 | Foerster |
| 2004/0267313 A1 | 12/2004 | Amery et al. |
| 2005/0125035 A1 | 6/2005 | Cichocki, Jr. |
| 2005/0149119 A1 | 7/2005 | Koyfman et al. |
| 2005/0247320 A1 | 11/2005 | Stack et al. |
| 2005/0267528 A1 | 12/2005 | Ginn et al. |
| 2006/0025818 A1 | 2/2006 | Ferguson |
| 2006/0030883 A1 | 2/2006 | Cichocki, Jr. |
| 2006/0121274 A1 | 6/2006 | Capurro |
| 2006/0253126 A1 | 11/2006 | Bjerken et al. |
| 2006/0253127 A1 | 11/2006 | Bjerken |
| 2007/0005110 A1 | 1/2007 | Collier et al. |
| 2007/0060932 A1 | 3/2007 | Stack et al. |
| 2007/0118151 A1 | 5/2007 | Davidson |
| 2007/0134305 A1 | 6/2007 | Zilberman |
| 2007/0260279 A1 | 11/2007 | Hotter et al. |
| 2007/0276432 A1 | 11/2007 | Stack et al. |
| 2008/0065122 A1 | 3/2008 | Stack et al. |
| 2008/0082113 A1 | 4/2008 | Bishop et al. |
| 2008/0154266 A1 | 6/2008 | Protopsaltis et al. |
| 2008/0183272 A1 | 7/2008 | Wood et al. |
| 2008/0281355 A1 | 11/2008 | Mayer et al. |
| 2009/0024151 A1 | 1/2009 | Shalaby et al. |
| 2009/0024162 A1 | 1/2009 | Shalaby et al. |
| 2009/0035572 A1 | 2/2009 | Hotter et al. |
| 2009/0104243 A1 | 4/2009 | Utkhede et al. |
| 2010/0241146 A1 | 9/2010 | Stack et al. |
| 2011/0054524 A1 | 3/2011 | Beevers et al. |
| 2013/0197574 A1 | 8/2013 | Mayer et al. |

FOREIGN PATENT DOCUMENTS

| | | |
|---|---|---|
| CN | 104155479 | 11/2014 |
| EP | 0328401 A1 | 8/1989 |
| EP | 1284756 A1 | 2/2003 |
| EP | 1199036 B1 | 2/2007 |
| JP | 48-023753 U | 3/1973 |
| JP | 59-034264 A | 2/1984 |
| JP | 63-075194 A | 4/1988 |
| JP | 01-138447 A | 5/1989 |
| JP | 10-500319 A | 1/1998 |
| JP | 2000-125855 A | 5/2000 |
| JP | 2003-019196 A | 1/2003 |
| JP | 2003-265169 A | 9/2003 |
| JP | 2005-177499 A | 7/2005 |
| JP | 2005-520066 A | 7/2005 |
| JP | 2006-515783 A | 6/2006 |
| JP | 2007-515212 A | 6/2007 |
| JP | 2008-539842 A | 11/2008 |
| WO | 95/25549 A1 | 9/1995 |
| WO | 96/03084 A1 | 2/1996 |
| WO | 98/22155 A1 | 5/1998 |
| WO | 03/78705 A1 | 9/2003 |
| WO | 2004/066847 A1 | 8/2004 |
| WO | 2005/055836 A2 | 6/2005 |
| WO | 2006/117398 A2 | 11/2006 |
| WO | 2010/052005 A1 | 5/2010 |
| WO | 2013/130547 A1 | 9/2013 |

OTHER PUBLICATIONS

Winkler et al. "Effect of suture material on tensile strength and complication rate in abdominal fascial defects repaired with acellular dermal matrix," Hernia, Feb. 2008, vol. 12, Issue 1, pp. 33-38.
Tongkui Cui, Yongnian Yan, Renji Zhang, Li Liu, Wei Xu, and Xiaohong Wang. "Rapid Prototyping of a Double-Layer Polyurethane-Collagen Conduit for Peripheral Nerve Regeneration". Tissue Engineering Part C: Methods. Mar. 2009, 15(1): 1-9. doi:10.1089/ten.tec.2008.0354.
Muffly et al., "Minimum Number of Throws Needed for Knot Security," Journal of Surgical Education, Original Reports, vol. 68, No. 2, Mar./Apr. 2011, pp. 130-133.
Muffly et al. "Tensile strength of a surgeon's or a square knot", J Surg Educ. Author manuscript (PMCID: PMC4167833), published as J Surg Educ. 2010, vol. 67, No. 4, pp. 222-226.
International Search Report for International Application No. PCT/US2013/027943, dated May 14, 2013, 5 pages.
International Preliminary Report on Patentability for International Application No. PCT/US2013/027943, dated Sep. 2, 2014, 7 pages.
Ind et al. "Influence of training on reliability of surgical knots", British Journal of Obstetrics and Gynaecology, Oct. 2001, vol. 108, pp. 1013-1016.
Harris et al.,"Fibroblast Traction as a Mechanism for Collagen Morphogenesis", BIOSIS Database record abstracting NATURE (London), 290,5803, 249-251, 1981.
Garvin et al., "Novel System for Engineering Bioartificial Tendons and Application of Mechanical Load". Tissue Engi neering, vol. 9, No. 5, pp. 967-979, 2003.
Depuy Mitek, Orthocord Suture, Brochure, Rev. B Jul. 2004, 2 pages.
D'Aversa et al.,"Tensile Mechanical Property Evaluation of Two Absorbable Sutures:Effects of Size and Types," [online],[retrieved on Jul. 15, 2015]. Retrieved from the internet, URL:http://2015.biomaterials.org/sites/default/files/abstracts/310.pdf>.
Cui et al, Rapid Prototyping of a Double-Layer Polyurethane-Collagen Conduit for Peripheral Nerve Regeneration, Tissue Engineering; Part C, vol. 15, No. 1. 2009, pp. 1-9.
Brochure for ORTHOCORD Suture, DePuy Mitek, Inc., 2004.

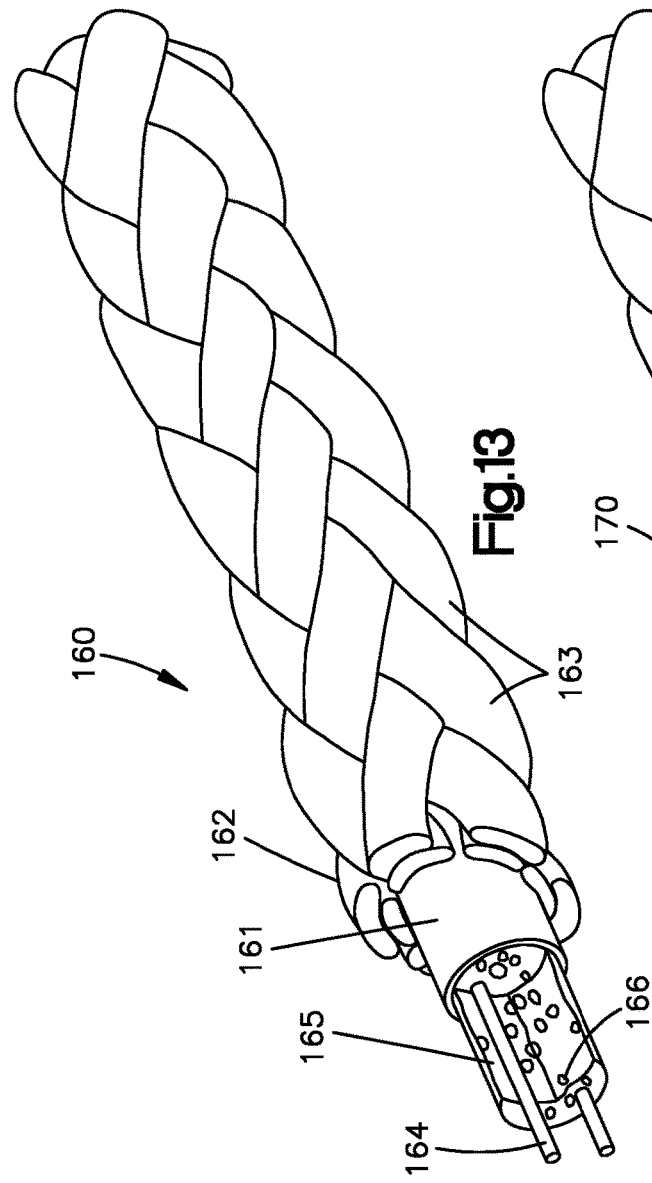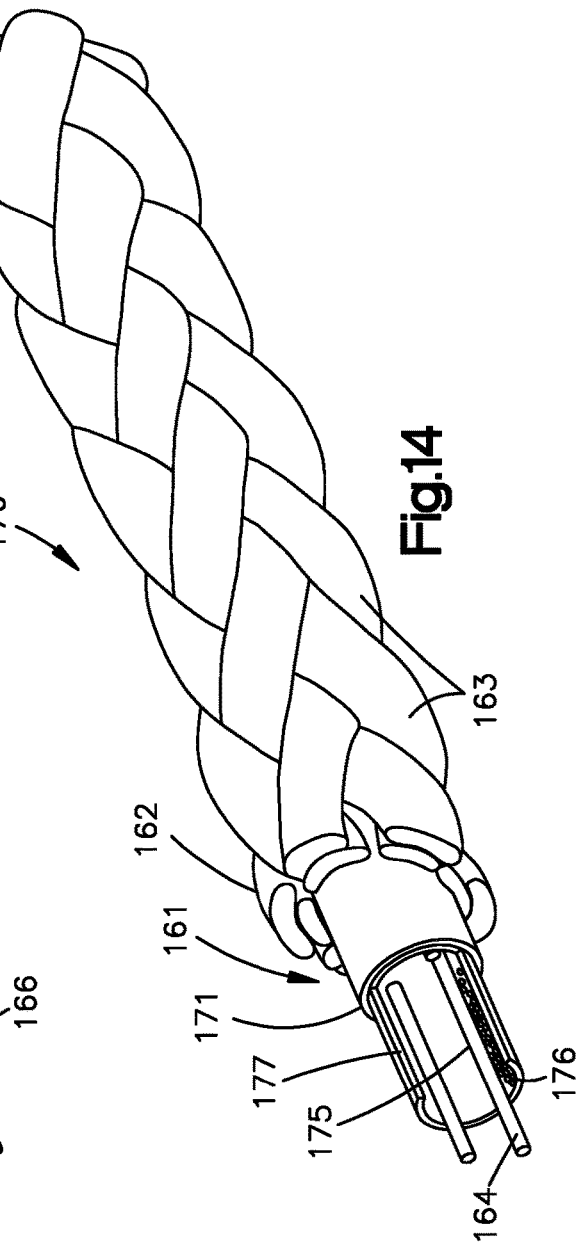

JOINING ELEMENT

CROSS REFERENCE TO RELATED APPLICATIONS

This application is a continuation application of U.S. Appl. No. 13/800,889, filed Mar. 13, 2013, now U.S. Pat. No. 9,757,121, which is a divisional application of U.S. Appl. No. 11/913,656, filed Jun. 12, 2008, now U.S. Pat. No. 8,870,915, which is a 371 application of PCT/EP2006/062061 filed May 4, 2006, which claims priority to Swiss Application No. SE 0834/05 filed May 4, 2005, each of which is hereby incorporated by reference in their entirety.

TECHNICAL FIELD OF THE INVENTION

The invention relates to a joining element, especially a suture material, especially for surgical purposes, but also relates to a two-dimensional or three-dimensional textile structure, especially also for technical use for joining technical structures, for example.

PRIOR ART

In the event of ligaments or tendons rupturing, a problem that still remains largely unresolved is that of securing a tendon for example to a bone in such a way that the connection does not come loose under the effect of loading. One of the problems is that the loads that are exerted on a joining element between bone and tendon are very different. Over long periods of time it is desirable for the joining element to contract, that is to say for the joining element between bone and tendon to tension. It is also possible to have a system with a high degree of damping. Movements on the part of the patient may subject the joining element to rapidly increasing high loads, under which the connection must not fail, which means that, in the event of short-lasting loads on the tissues connected by the proposed joining element, the healing is not impaired to a clinically significant extent.

The prior art achieves the connection of different structures (for example tendon to bone) in the body typically by means of suture material, which is rigid and passively transmits the forces that arise. Larger surfaces are bridged (for example in the case of a fascial gap) by means of a two-dimensional load bearer, for example a mesh that is connectable. Connectable is to be understood as covering a number of methods, for example, but not exclusively, suturing, stapling or adhesion.

The use of shape-memory polymers is known, for example, from EP 1 284 756, in order to structure muscle, cartilage or nerves in tissue engineering.

In order to bridge more complex defects, planar or three-dimensional structures are also of interest (for example a pouch around an organ). An unresolved problem here is how to avoid loosening or tearing of a connection in the tissue. The invention is intended to remedy this situation.

Moreover, in the context of securing goods, in particular in the open air, a disadvantage is that textile-based ropes loosen under the influence of moisture, such as dew and rain, and therefore no longer properly hold packages or containers together.

SUMMARY OF THE INVENTION

Starting out from this prior art, the object of the invention is to make available a joining element of the type mentioned at the outset, which contracts over long periods of time, but which on the other hand is rigid under short-term rapidly increasing loads.

According to the invention, this object is achieved by a joining element according to claim 1.

A short-lasting or fairly short-lasting tensile load is considered to be one that builds up and/or reduces over the course of less than 1 minute, in particular one that is shorter than 10 seconds. In applications of the invention as repair material for the apparatus of locomotion in humans, this means for example the load exerted, during walking, on the joining material that connects the muscles to the bone.

Contraction is also understood as a relaxation of the material, for example in the sense of a change in shape of the first material or a decomposition. Such a change in shape can also be regarded as a deformation, but one that occurs without application of an external force. Moreover, the second material is able to swell and be compressed by the first material transverse to its longitudinal direction, such that a contraction takes place. In particular, the swelling of a core material in the first material can enforce a change in shape, for example by changing the angle of intersection in the braid, which results in the shortening of the joining element.

The second material is also able to diffuse out of the first material, such that the element shortens, or the second material can comprise threads that are initially stretched or oriented parallel to the longitudinal direction of the joining element, and said relaxation takes place as a result of deformation of said threads in the first material. Threads describe in this context molecules and molecule structures.

In packagings and containers for goods, ropes having the features of the invention can ensure that the packaging remains securely held by the surrounding ropes, despite the effects of weather.

The invention permits the use of a method for stimulating healing and for stimulating biological transformation and regeneration processes of soft-tissue parts relative to one another, such as tendons, ligaments, fascias, organ cavities, general connective tissue, vessels, heart valves, cartilage tissue, etc., or of soft-tissue parts relative to bone, by the gentle, active, partially dynamic compression that can be achieved by using the material described here.

BRIEF DESCRIPTION OF THE DRAWING

The invention is described below in more detail with reference to the drawings, in which:

FIG. 13 shows a schematic view of a part of a joining element with a thread with solid core according to an illustrative embodiment of the invention, FIG. 14 shows a schematic view of a part of a joining element with a thread with tubular core according to an illustrative embodiment of the invention.

DETAILED DESCRIPTION OF ILLUSTRATIVE EMBODIMENTS

Figure 1:
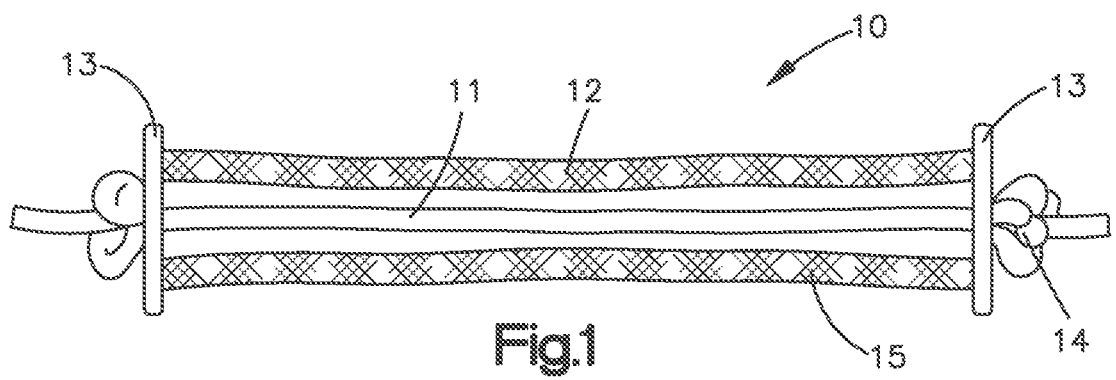
FIG. 1 shows a schematic view of part of a joining element shortly after a test use in vitro or in vivo, that is to say after an implantation, according to a first illustrative embodiment of the invention.

FIG. 1 shows a schematic representation of a part 10 of a joining element, which comprises a pretensioned core 11 surrounded by a jacket 12. The jacket 12 is composed of a rigid material, which is compressed under the effect of chemical and physical processes that take place over the course of time and are described below. The resulting force that triggers this compression process is the force resulting from the pretensioning of the core minus the tensioning force acting on the thread from the environment (for example the tensioning force applied during stitching). As the tensioning force exerted on the thread by the environment decreases, the resulting compressive force acting on the jacket increases. This favors the compression of the jacket, resulting in an accelerated contraction of the thread or of the textile structure formed from the latter. This results in a tensioning of the thread or of the textile structure until an equilibrium is once again established between the forces described above, or the jacket is able to support the compressive force acting on it, without slow compression.

The material for the jacket is characterized in that it permits controlled plastic deformations over a defined period of time, i.e. the material has a distinct yield point and behaves substantially elastically below the yield point. This means that the main component of the material should have a glass transition temperature above body temperature or should have a high crystallinity and additionally has a high degree of fracture toughness. Typical representatives of this class of materials are, for example, blends or copolymers of structural polymers with a Tg distinctly above body temperature and polymers with a Tg distinctly below 0° (blend: polylactides with trimethylene carbonates, copolymer: polyhydroxybutyrate with polyhydroxyvalerate). However, this function can also be performed by highly crystalline polymers such as PE, polyamides or polyesters, in which case the structure of the envelope would have to be provided with defined yield points, for example by local thinning of the cross section, incorporation of reinforcements and kinks, or local periodic variation of the modulus of elasticity by variation of the polymer orientation. At the ends of this part 10 of the joining element there is in each case a joining construction 13, for example a mesh, with which the jacket 12 is woven. The core 11 is routed through this mesh 13 and, for example, knotted 14. The core 11 itself is composed of a flexible material. Examples of materials for the core are preferably materials of an elastomeric nature and with minimal tendency to creep, typical representatives of which are crosslinked polymers such as silicones or polyurethanes, which can also be composed of degradable components if complete degradation of the thread is sought. In the rest position, the core 11 is shorter than the distance between the joining constructions 13, such that the inserted core 11 in the view in FIG. 1 is pretensioned. This is indicated by the arrows 15. Since the jacket 12 is rigid, the joining constructions 13 are kept spaced apart despite the effect of the spring tension of the core 11.

The functions of the core and jacket as described here can also be interchanged, i.e. before processing the jacket is pretensioned and the core is acted on by pressure.

It is also possible for the pretensioning to be applied only after the processing (for example after the stitching in the case of the thread).

A joining element, in particular a suture material for wound treatment, for example also a wide band, can be made up of many such parts 10 of joining elements, in which for example many joining elements are arranged alongside one another and in succession, in order to form a band that can be processed. The joining elements are advantageously surrounded in their entirety by an envelope with controlled kinking behavior. However, it may also be possible for each individual element to be surrounded by such an envelope, particularly if the whole construction is to be as flexible and formable as possible.

If a large force quickly builds up on such a band and abates again after a certain time, for example a force that builds up in tenths of seconds, possibly lasts for a few seconds and then returns to zero, the rigid jacket 12 then holds the individual parts 10 in position and thus also the band and, consequently, the organs connected thereto, for example a tendon and a bone.

Figure 2:
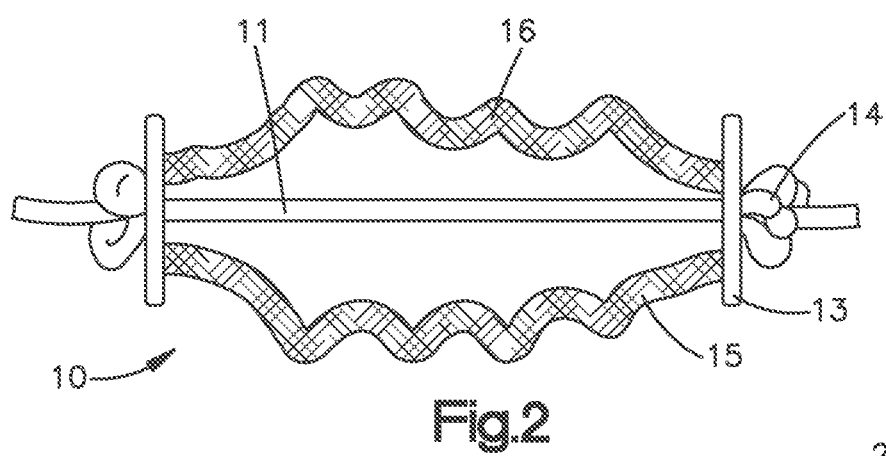
FIG. 2 shows a schematic view of part of a joining element after a longer period of time since the start of said use according to FIG. 1.

FIG. 2 now shows the development of a part 10 of a joining element over a long period of time, for example over several weeks. After a long period of time, possibly interrupted by forces of the short-lasting type mentioned above, the jacket 12 deforms, here designated as changed jacket by reference number 16. By means of the pretensioning effect of the core 11, the joining constructions 13 move toward one another, and the band made up of the parts 10 of the joining elements contracts. This results in a change in length of up to 80 percent from the original length.

Figure 3:
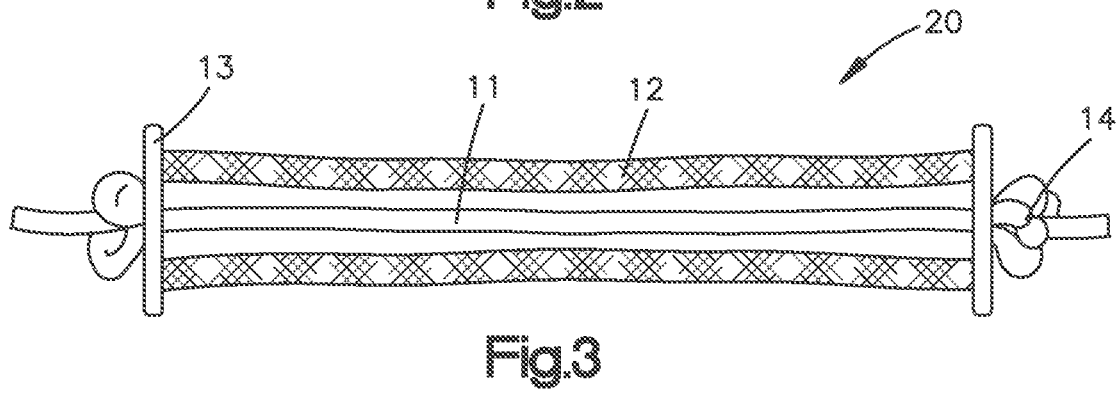
FIG. 3 shows a schematic view of part of a joining element shortly after a test use in vitro or in vivo, that is to say after an implantation, according to a second illustrative embodiment of the invention.
Figure 4:
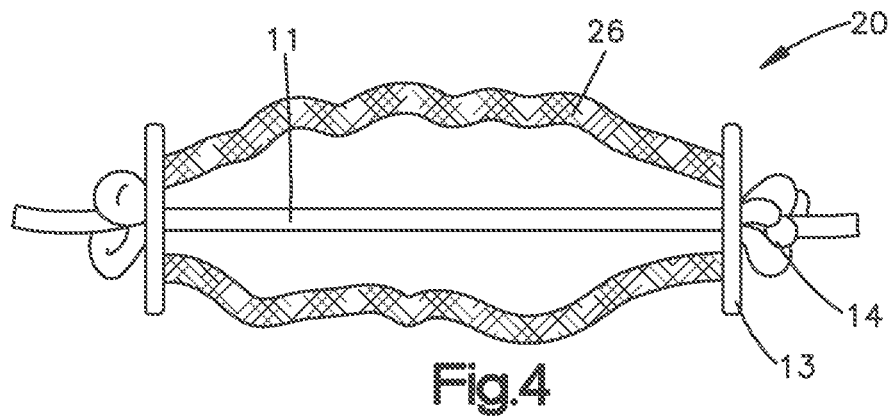
FIG. 4 shows a schematic view of part of a joining element after a long period of time since the start of said use according to FIG. 3.

Instead of a deformation of the jacket 16, the jacket 22 according to another embodiment can also structurally decompose, for example by the at least partial use of the aforementioned biodegradable polymers, that is to say at least part of the material initially loses some of its modulus of elasticity and thus its stability against kinking, as a result of the uptake of water and the incipient hydrolysis of the incorporated biodegradable polymers, but at the same time gains in terms of its plastic deformation capacity. As the degradation proceeds, this results in loss of mass and physical breakdown. This is shown in FIG. 3 at the start of use and in FIG. 4 after a long period of time. Similar features are in each case provided with the same reference numbers in all of the drawings.

The part 20 of a joining element is provided with a jacket 22, which loses its structural integrity over the course of time. This can be seen from the thinner jacket 26 in FIG. 4. The degrading jacket 26 thus offers less resistance to the flexible core 11, and the distance between the joining constructions 13 becomes shorter. If, however, rapid tensile or impact forces act on the joining element 20 during this process, then it again reacts rigidly, because the stiffness properties of the jacket 22 have not in principle been changed by the deformation, particularly in relation to its resistance against rapid stressing, they are not macroscopically different (departing from the only schematic representation in the FIG.), and have only become weaker relative to the core 11. This involves in particular the elastic properties of the jacket material that are of relevance in short-term stressing.

Impact forces can be taken up if planar or three-dimensional bodies are formed from the joining elements, which bodies have a buckling or kinking stability defined by their cross section. This can be achieved, for example, by a sheet of interconnected rotationally symmetrical threads or by the fact that the interior of the joining element is elongated with an oval or ellipsoid cross section.

In an illustrative embodiment not shown in the drawings, the joining element 10 or 20 can also have a rigid core and a pretensioned jacket. The function according to FIGS. 1 to 2 and 3 to 4 remains the same, however. The important point is that each part 10, 20 does not react to rapid load changes, in other words remains rigid, while it contracts over the course of time.

It is clear that such one-dimensional elements can also be given a two-dimensional or three-dimensional arrangement, such that contracting textile structures are obtained. It is also possible for these materials to be provided with resorbable constituent materials, such that these materials can finally disintegrate.

Figure 5:
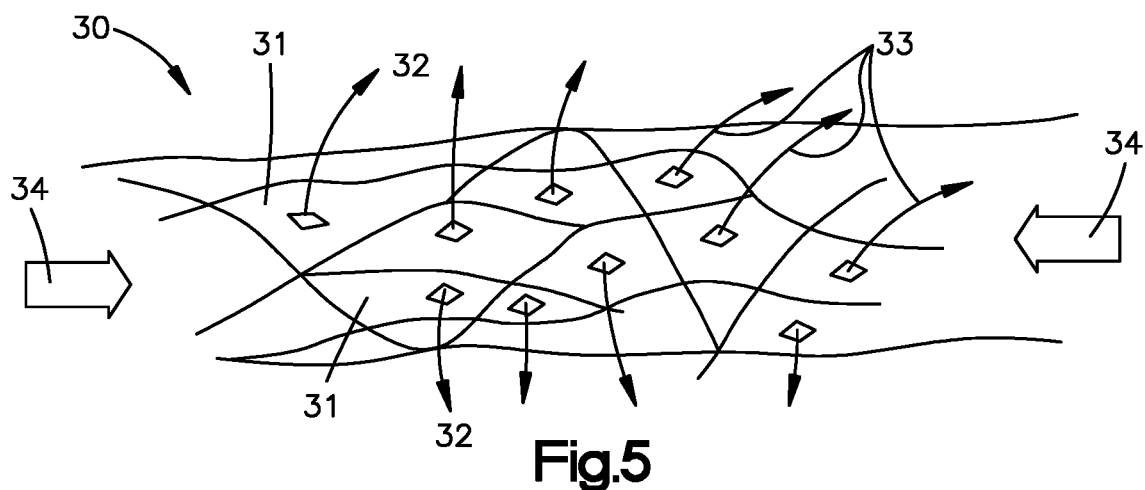
FIG. 5 shows a schematic view of a joining element shortly after a test use in vitro or in vivo, that is to say after an implantation, according to a third illustrative embodiment of the invention.
Figure 6:
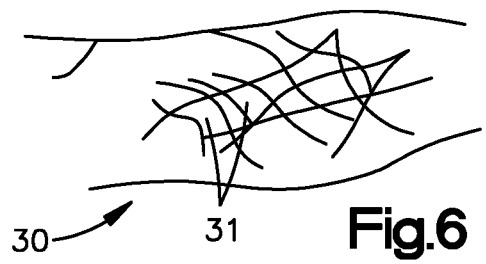
FIG. 6 shows a schematic view of the joining element after a long period of time since the start of said use according to FIG. 5.

FIG. 5 shows a third illustrative embodiment of a joining element 30. The joining element 30 is made up of a multiplicity of adjacent molecules 31 (core polymer) that have an incorporated lubricant 32. The molecules can, for example, be polymeric macromolecules of known biocompatible polymers. The so-called lubricant, which acts for example as a plasticizer, can involve in particular, but not exclusively, a solvent for the core polymer or also substances with a high degree of solubility in the core polymer, this substance having to be biocompatible in the released doses. It can involve low-molecular-weight solvents such as acetone or alcohols, or also N-pyrrolidone or dimethylsulfonamide (DMSO), which are known to be tolerated in relatively high doses. Gradually, for example over periods of weeks, the lubricant 32 leaves the thread, as is indicated by reference number 33 for the arrows; in other words the lubricant is diffused out. The kinetics of the diffusion are on the one hand determined by the molecular interactions between the core polymer and the lubricant, and on the other hand the diffusion behavior can be controlled by the application of organic (for example another polymer of low solubility for the lubricant) or inorganic (for example CVD layers such as plasma-polymerized PMMA or SiOx or amorphous diamond-like layers), biocompatible barrier layers. In this way a force acts in particular along the arrows 34. The joining element 30 thus converts to a contracted state according to FIG. 6, in which each molecule 31 takes up less space. These joining elements 30 can be similar to threads, but can also be composed of several textile filaments.

Figure 7:
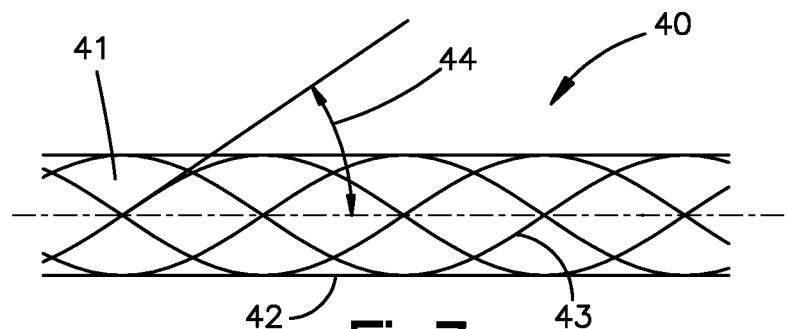
FIG. 7 shows a schematic view of a joining element shortly after a test use in vitro or in vivo, that is to say after an implantation, according to a fourth illustrative embodiment of the invention.

FIG. 7 shows a fourth illustrative embodiment of a joining element 40. The joining element 40 comprises a core 42 surrounded by a jacket 41. The core 42 is a swellable material, for example as mentioned below. The jacket 41 is composed in particular of a mesh, for example of threads 43 arranged helically around the core 42, in particular braided or interlacing threads 43, in particular from the group of known degradable and nondegradable polymers which have been described and processed for suture materials and which typically are used in surgical suture materials, for example stretched polyesters, polyamides, polyolefins, polyaramides, expanded or densely halogenated polymers or high-strength ladder polymers such as polyetherether ketone, captones. FIG. 7 shows the joining element 40 in the rest state, where the threads 43 are oriented for example at an angle 44 of 30 degrees with respect to the longitudinal direction of the joining element 40. The angle can in its initial state be between 5 and 50 degrees for example, in particular from 10 to 40 degrees, and is preferably 20 to 35 degrees. Thus, the illustrative embodiment depicted here falls midway in this interval.

Such a joining element 40 does not react to rapid changes in force. By contrast, a swelling of the core 42 caused by chemical and physical processes leads to a thickening of the core 42 surrounded by the thread 43. In this way, the angle 44 with respect to the longitudinal direction of the joining element 40 changes to a new angle 45, for example of 48 degrees. The mesh 46 is thus imparted a greater diameter and shortens, as does the entire joining element. When made up of braided threads, the mesh is designated as a braid. This term can accordingly replace the word mesh throughout the application.

The swelling process can be achieved for example by an osmotic core 42, that is to say a core 42 which with an osmotically active substance (for example salt, particulate form of a water-soluble substance (for example saccharides) or highly concentrated solution of these substances in an elastic tube), which accordingly takes up water.

Figures 7A, 8:
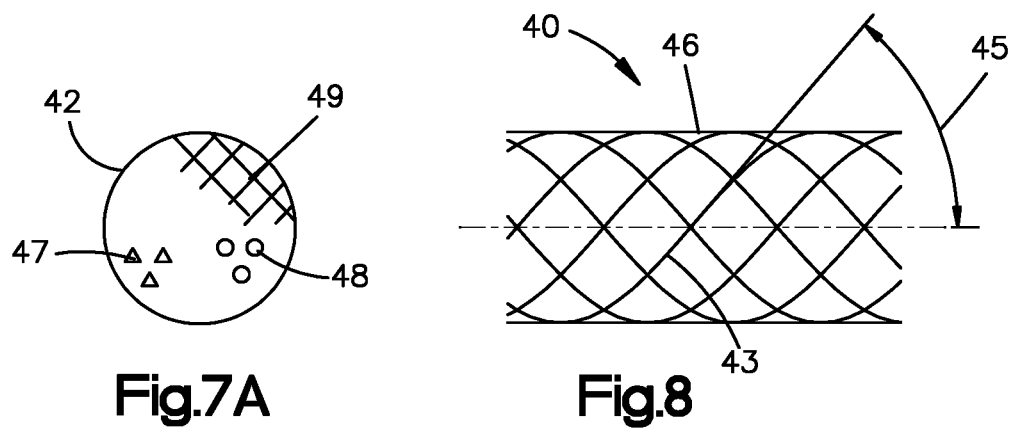
FIG. 7A shows a cross-sectional view of the joining element illustrated in FIG. 7.
FIG. 8 shows a schematic view of the joining element after a long period of time since the start of said use according to FIG. 7.

For example, as is represented very schematically in FIG. 7A, the core 42 can comprise a filamentary polymer material (not degradable, or also completely or partially degradable), for example a thermoplastic elastomer (polyurethane, polyester), a crosslinked elastomer (silicone, polyurethane, elastin, collagen) or a gel (polyethylene glycol, alginate, chitosan) in which salt crystals 47 are incorporated, wherein the particulate substance can advantageously have a concentration of between 5 percent and 75 percent by volume in the polymer depending on the particle size, particle size distribution and state of agglomeration. When nanoscopic particles are used, however, the high particle count means that concentrations of less than 1% are already effective. The polymer thread can be extruded from the melt or from the solution, and the particles are co-extruded or admixed to the polymer mass before extrusion. They can also have a concentration of 25 to 60 percent. Since individual alveoli form around the particles as the surrounding liquid is taken up, the strength of the core (the thread strength is determined by the properties of the surrounding filaments) is directly dependent on the concentration of the particles.

In another illustrative embodiment, a tube can be provided with a membrane, for example a PU membrane, of 10 to 200 micrometers into which the expanding material or the osmotically active substance or its highly concentrated solution is directly filled. Therefore, except for the packing density, 100 percent of the volume is filled with the osmotically active substance or the salt. The tube can be made of PUR, siloxane, PEG or other permeable, in particular semipermeable products in the form of osmotic, elastic or plastic and geometrically extendible membranes (e.g. stretching of axial folds, pleats or undulations). In particular, the tube can be narrowed at regular intervals in order to form segmented chambers. This means that the overall thread can be cut to any desired length, without substantially influencing the described effect.

The osmotically active substances can include biocompatible inorganic salts and aqueous solutions thereof, for example sodium chloride (NaCl) or calcium chloride, calcium carbonate, tricalcium phosphate, or organic, osmotically active molecules can be used, for example low-molecular-weight polysaccharides such as dextran. To improve handling and to further influence the kinetics of osmosis, the osmotically active substances can also be embedded in a biocompatible gel or hydrogel (for example from the group of alginates, chitosans or copolymers thereof, polyacrylates, polyethylene glycol, etc.) or, as explained above, in an elastomer. An effect whose action is comparable in principle to the osmotically active substances can also be achieved by sole use of hydrogels. According to Fick's laws, particular importance is attached to the membrane surrounding the swelling system, which membrane critically influences the kinetics of osmosis by virtue of its permeation and diffusion properties for $H_2O$, and also by virtue of its thickness. The membrane can of course be made up of several layers or can also be provided with stable or soluble diffusion-inhibiting layers. If hydrogels are used, such a membrane-like property can also be achieved by means of a crosslinking density that increases considerably toward the outside. The concentration differences effecting osmosis are to be achieved between thread core and surrounding blood or interstitial and/or intrastitial fluid of the patient.

The braided arrangement of the threads 43 can be obtained using textile threads, as are typically used for degradable or nondegradable monofilament or multifilament suture materials, for example stretched or textured polyesters, polyamides, polyolefins, polydioxanones. The suture material can be constructed from a swell core surrounded by the braided threads and also from several interwoven swellable threads each in turn surrounded by a threaded braid. The filament diameters are in line with the prior art in terms of the fineness of the core that is to be surrounded and in terms of the choice of a monofilament or multifilament covering yarn (0.2-200 micrometers). This shortening mechanism, acting like a sliding lattice, can also be achieved analogously with a thread equipped with a swell core, with a swelling coating of the structural filaments, in particular of the structural filaments forming the braid or additionally axially extending structural filaments. As has already been stated concerning the other illustrative embodiments, contracting two-dimensional or three-dimensional textile structures can also be created using said thread materials.

In other words, the joining element 40 is given long-term degrees of freedom, with the result that the material slowly relaxes or contracts without application of force. At a peak load, by contrast, the joining element 40 reacts rigidly. Of course, in accordance with the prior art, all materials or material surfaces coming into contact with the biological tissue can be chemically, biochemically or biologically functionalized, for example by adsorption, grafting or release of biologically active substances such as growth factors, inflammation inhibitors, cytokines, receptors or receptor sequences, antibiotics, or substances that have an antibiotic, cytostatic, bactericidal or bacteriostatic effect.

FIG. 7A shows a further functionalization, according to the invention, of the joining element. The swelling core 42 comprises vesicles 48 charged with active substance, or comprises interstitially dissolved active substances 49, which are thus incorporated between polymer chains. By means of the swelling, the pressure on the vesicles and on the dissolved active substances increases. Therefore, active substance can be actively driven out of the core. By varying the radial distribution density of the vesicles, it is possible to obtain a time-controlled release profile, which is of course also influenced by the swelling pressure that builds up. If the core is provided with, as described above, a diffusion-controlling membrane, the flow of substance out of the core can additionally be influenced by the transport properties of the membrane that are dependent on concentration and on chemical activity. The reference numbers 47, 48 and 49 have, for sake of clarity, been indicated at different locations of the core 42. In principle, the salt particles 47 can be distributed isotropically in the core. The active substances can advantageously be provided either in vesicles 48 or be interstitially dissolved, but in both configurations, and in contrast to the simplified representation, there is an isotropic distribution across the core.

In other words, a swelling effect will be achieved by hydration of a macromolecule structure. A tubular elastic membrane is fitted in a mesh sleeve made up of rigid threads that wind in a helical formation around the tube. Tensile forces are transmitted via this mesh sleeve. In the interior of the tube there is a saturated salt solution. Mesh sleeve and membranes are placed in an isotonic solution. By means of a chemical/physical process, a concentration balance takes place until a state of equilibrium is obtained. As a result of the solvent being taken up, a considerable pressure builds up in the interior of the elastic tubular sleeve and results in a swelling of the tube. A force equilibrium is established between the internal pressure and a tensile force that is applied to the mesh sleeve or braided sleeve in the axial direction. The mesh sleeve acting as a sliding lattice contracts.

A simulation has been conducted in order to calculate the longitudinal contraction force and the changes in dimension caused by the osmotic pressure at a given concentration difference (Δc) [mol/l] on both sides of the membrane for 310 degrees Kelvin:

| | |
|---|---|
| Thread diameter at start $d_0$ | $7 \times 10^{-4}$ m |
| Starting angle α | 60° |
| Thread angle to tension direction β | 90-α° |
| Concentration body $C_{blood}$ | 0.296 mol/l |
| Saturation concentration (NaCl) $C_{saturation}$ | 6.15 mol/l |

The osmotic pressure Π [Pa] for ideally diluted solutions can be set out in a simplified manner as follows:

$$\Pi = \Delta c \cdot R \cdot T = (c_{saturation} - c_{blood}) \cdot R \cdot T$$

Radial tension $\sigma_{radial}$ [N/m] with boiler formula:

$$\sigma_{radial} \frac{\pi \cdot d_{thread}}{2}$$

Radial force ($f_{radial}$) [N/m] from tension ($\sigma_{radial}$):

$$(\sigma_{Radial}) = \frac{F_{radial}}{\ell_{circum.}} = \frac{\Pi \cdot d_{thread}}{2} = f_{radial}$$

Thread diameter ($d_{thread}$):

$$(d_{thread}) = d_0 \cdot \frac{\cos \alpha}{\cos \alpha_0}$$

Ratio of radial force ($F_{radial}$) to longitudinal force ($F_{long}$):

$$F_{long.} = F_{radial} \cdot \tan \alpha$$
$$= f_{radial} \cdot \tan \alpha \cdot \ell_{circum.}$$
$$= \frac{\Pi \cdot d_{thread}}{2} \cdot \tan \alpha \cdot d_{thread} \cdot \Pi$$

$$F_{long.} = \frac{\Pi \cdot d_{thread}^2}{2} \cdot \tan \alpha \cdot \pi$$
$$= \frac{(c_{saturation} - c_{blood}) \cdot R \cdot T}{2} \left( d_0 \cdot \frac{\cos \alpha}{\cos \alpha_0} \right)^2 \cdot \tan \alpha \cdot \pi$$

Pressure force ($F_{pressure}$) [N]:

$$F_{pressure} = \Pi \cdot A = \Pi \cdot \frac{d_{thread}^2}{4}$$

Relative length (l) [%]:

$$= \frac{\sin \alpha}{\sin \alpha_0}$$

Relative volume (V) [%]:

$$V = l \cdot d_{relative}$$

Resulting length-contraction force ($F_{res}$) [N]:

$$F_{res.} = F_{long.} - F_{pressure}$$

At a difference of Δc=5.8 mol/l, it has been found that the resulting length-contraction force is maximum at a defined thread angle of approximately 30° and at the starting dimensions. As the volume increases, the surface area and thus the pressure force ($F_{pressure}$) becomes greater, such that the resulting length-contraction force decreases. The proportion of the radial force becomes greater than the longitudinal component starting from an angle of 45°. The desired minimum of the longitudinal force is achieved in this example at a thread angle of 48°. At this point, the thread has shortened by slightly more than 20%. A corresponding representation is shown in FIG. 11.

Figure 9:
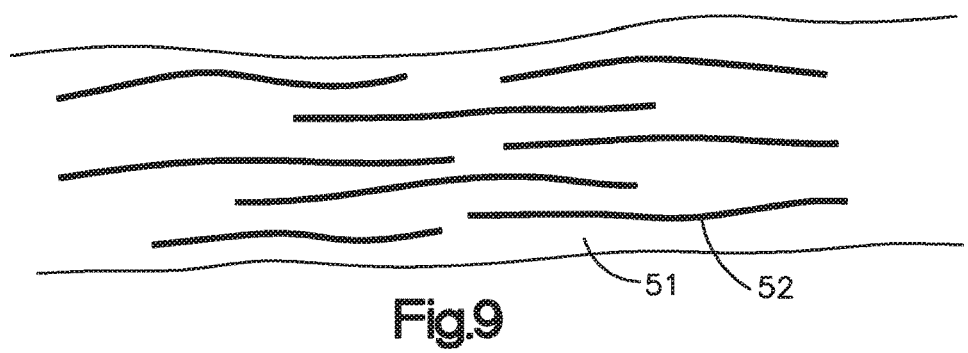
FIG. 9 shows a schematic view of a joining element shortly after a test use in vitro or in vivo, that is to say after an implantation, according to a fifth illustrative embodiment of the invention.
Figure 10:
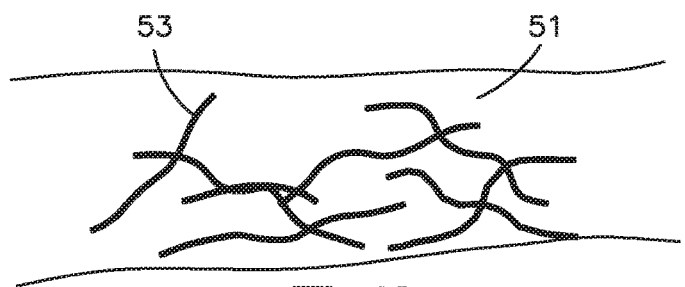
FIG. 10 shows a schematic view of the joining element after a long period of time since the start of said use according to FIG. 9.

FIG. 9 shows a schematic view of a joining element 50 shortly after a test use in vitro or in vivo, that is to say after an implantation, according to a fifth illustrative embodiment of the invention. The joining element 50 is a thread made up of a base material 51, for example composed of the customary degradable or nondegradable suture materials, in which thread molecules 52 are incorporated. The molecules 52 can for example be polymers with a glass-transition temperature well below body temperature, or polymers can be chosen which have a marked tendency to take up water and swell (for example polysaccharides, polyamides) or also polymers, or polymers whose previous crosslinking is reduced by the hydrolytic degradation of the crosslinking sites, such that the contractility of the molecules is increased, and which, for example by means of processing and their limited solubility in the base material, can form molecular strands or also mesoscopic structures, for example nematic structures.

The threads are stretched during production, such that the contractile thread molecules or phases 52 are oriented parallel to the longitudinal direction of the joining element 50. When a force is applied rapidly, that is to say a traction or impact, the joining element 50 reacts rigidly via the threads 52. Over a long period of time, for example several days and in particular several weeks, the thread molecules or phases 52 deform, in particular they contract and coil up or expand transverse to the original direction of stretching. In doing so, they leave the longitudinal orientation and thus become shorter relative to this longitudinal orientation. A comparable thread section thus becomes shorter. If, during this process, rapid traction or impact forces act on the joining element 50, it again acts rigidly, since the stiffness properties of the threads 53 have not basically been changed by the deformation. Although the modulus of elasticity of a coil structure is significantly less than that of an oriented, nematic structure, this structure, from the mechanical point of view, takes up only a small part of the short-lasting loads on the joining element 50. The stiffness is therefore not appreciably affected by such an impact-type load.

Figure 11:
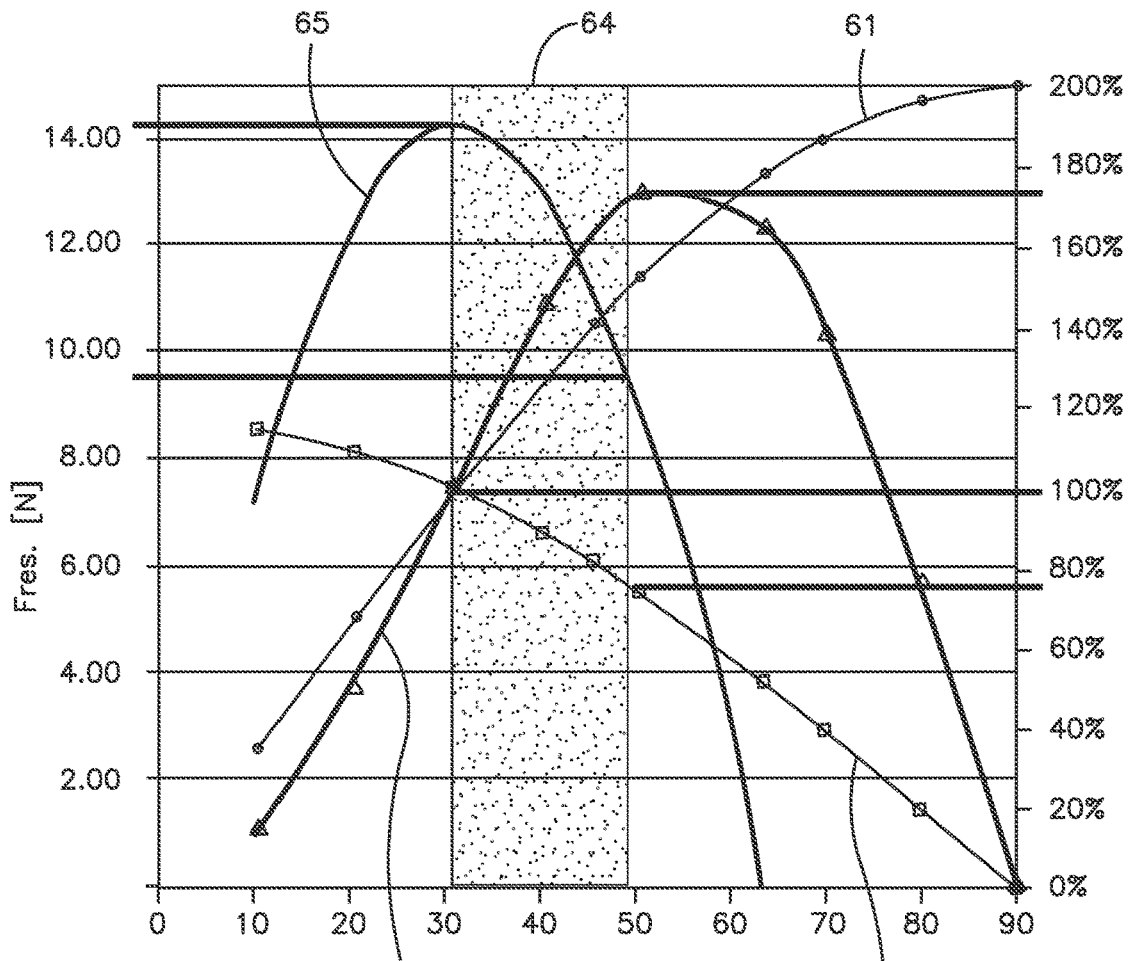
FIG. 11 shows a schematic diagram for an example of an area of use of a joining element according to the invention.

FIG. 11 finally shows, in a schematic representation, a diagram of an illustrative embodiment according to the invention, in particular an example of a range of use of a joining element according to the invention. The thread angle with respect to the tension direction is plotted in degrees on the X-axis, which angle has been provided with the letter β in the above formulae. On the Y-axis, the force $F_{res}$ in newtons is plotted on the left-hand side, while the right-hand side shows the relative diameters (reference number 61), lengths (reference number 62) and volumes (reference number 63) in percent. The thread angle range defined by the box 64 covers a change in volume of over 50 percent. The corresponding force curve 65 shows a not all too asymmetrical force distribution, and thus not too great a drop, around the maximum load of the thread element.

A method for treating tissue and prosthetic material comprises the method step of connecting tissue and/or prosthetic material with a joining element according to the invention. Prosthetic material can include thread or mesh material without needle, which is secured as a prefabricated thread loop on one or more suture anchors or similar implants. The prosthetic material can also include thread material with a needle, which is secured as a prefabricated needle with thread loop on one or more suture anchors or similar implants. In particular, a band produced from the thread material can also be connected directly to the bone or soft tissue, for example, by means of a staple or pin or nail.

The joining element, which shortens over the course of time, is used in the fixation of tendons or ligaments to bone. A further use of the joining element, which shortens over the course of time, in combination with suture anchors, secured fixedly or sliding, is as a loop or a connection between anchor retention plates (parachutes) or a connection between several anchors. The joining element, which shortens over the course of time, can also be used in mammals and other animals, in particular in humans.

In particular, the joining element, which shortens over the course of time, can be provided for surgical use in connection with the following applications: tendon reconstruction, in particular Achilles tendon reconstruction or rotator cuff reconstruction, shoulder stabilization operations on the glenoid, tendon transfers, for connecting tendons, fascias, ligaments or other soft-tissue parts, joint stabilization operations, for example on the joint capsule, joint stabilization operations, in particular acromioclavicular or sternoclavicular joint stabilization, collateral ligament reconstructions, for example on the knee, elbow or ankle, cruciate ligament reconstruction, closure of fascial gaps, hernia operations, wound closure in open-wound treatment, for example after fasciotomy, skin sutures, reconstruction of tendons, bones or soft-tissue parts on implants of all types, resorbable or nonresorbable, for example on prostheses or suture anchors, ligatures, fixation/suspension of uterus or bladder, suturing of intestine, stomach, bladder, vessels, trachea, bronchi or esophagus, and suturing of fascias.

The joining element, which shortens over the course of time, can be used as tissue. It can also be used as a pouch for enclosure of organs, for example the heart. The tissue can also be used for fascial gaps.

The tissue can be used as bridging graft for tendons or fascia defects. It can also be used for closure of skin defects, for example in combination with artificial or cultivated skin or other skin-closure materials, or serves as a cuff around vessels, for example in an aneurysm, around bile ducts or the gallbladder, around parts of the intestine, for example the stomach. Finally, the tissue can also be provided for external application, for example as support stockings, burns coverings for scar correction or the like. Moreover, the tissue can also serve as a bridging graft for several tendons at the same time, if these are connected to different sections, for example on the rotator cuff It may be particularly advantageous for the material to be provided in prefabricated form, that is to say in the form of the organs or organ parts that are to be replaced or augmented, for example as cruciate ligaments, tendons, retinacula, fascias, etc. Moreover, the thread material can be provided with functional surface structures, for example with barbs for fixation of soft-tissue parts. Finally, there is the connection of the thread material to bone suture anchors, sliding in the anchor or not sliding, for knotting or in a knotless configuration. It can be produced from non-resorbable, partially resorbable or completely resorbable materials. In order to distinguish between different properties, joining elements can be produced and used in different colors.

In addition to being used alone, they can also be provided in combination with rigid one-part or multi-part implants, for example with an inherently displaceable compression plate that contracts in a desired manner during contraction of the thread.

In addition to these uses, the joining element can also be used for the connection of technical objects, for example for the connection of textile sections or fastening elements generally. The description of the use of illustrative embodiments in medicine does not imply any limitation to this use.

Figure 12:
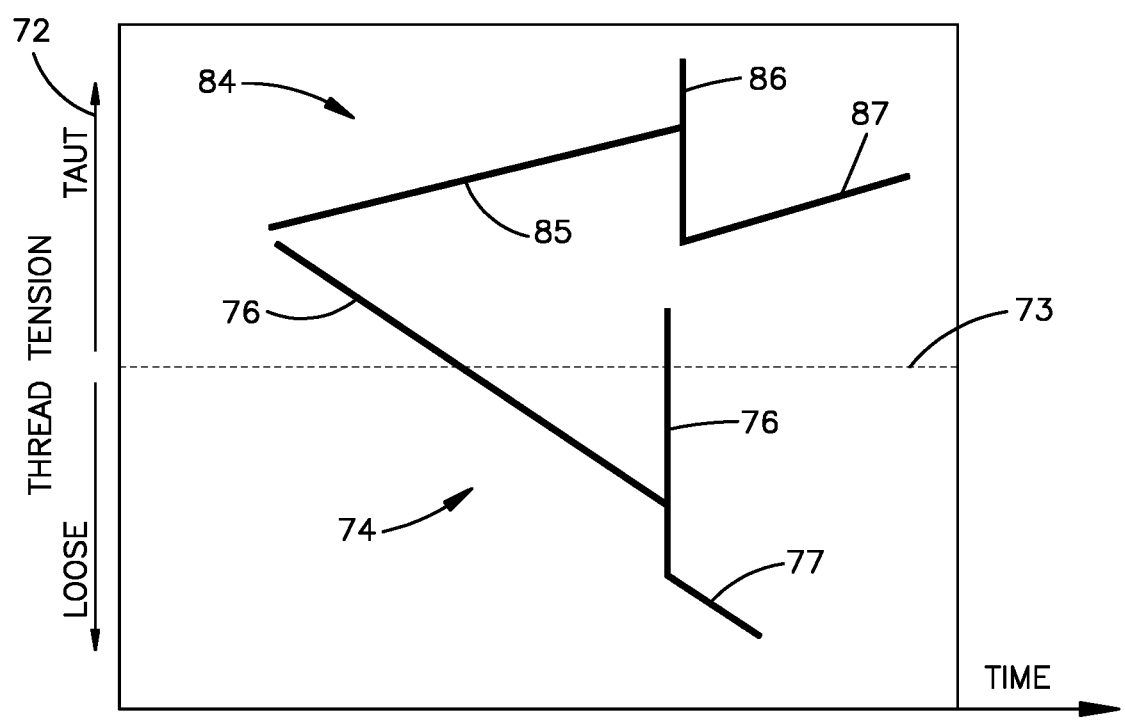
FIG. 12 shows a schematic diagram of the thread tension plotted against time for a joining element in the form of a thread according to the invention in a test use in vitro or in vivo compared to a conventional thread.

FIG. 12 shows a schematic diagram of the thread tension 72 plotted against time 71, for a joining element in the form of a thread 84 according to the invention in a test use in vitro or in vivo, compared to a conventional thread 74.

The broken line 73 indicates an arbitrary threshold above which a thread would be designated as taut (high thread tension) and below which a thread would be designated as rather loose (low thread tension).

The curve 74 relates to a conventional thread, the curve 84 to a thread according to the invention. Close to the starting time of an implantation for securing a ligament for example, the tensions of both threads are comparable. The conventional thread gradually loses tension, as is represented by the monotonic downward line 75. In the event of a fall 76, which can also be any inappropriate movement on the part of the person with the sutured ligament, there is a sudden increase in tension, whereupon the subsequent monotonic downward line 77 drops further to a still lower level.

By contrast, in the case of a thread 84 according to the invention, there is a monotonic increase 85 in the thread tension over the course of time. This is important, because a fall 86 of the same amplitude, here occurring at the same time as the fall 76, also leads to a loosening of the thread after the short-lasting increase in tension is removed. However, the drop is not so great that the tension after the event lies substantially below the starting tension. There is then a renewed tightening 87 of the thread, after which a higher tension value can again be achieved. This cycle can repeat itself several times in order to compensate for dislocations of the healing tissue parts until completion of the healing process, which is completed after several weeks, by contractile reunion of the tissue parts.

FIG. 13 shows a schematic view of a part of a joining element 160 with a thread with solid core according to an illustrative embodiment of the invention. This represents a special configuration. The thread 160 is composed of a core 161 and of a mesh sleeve 162. The mesh sleeve 162 is in this case made up of twelve braided filaments 163. The filaments are multifilaments that take up an oval space. In this way, it is possible for the braiding to completely cover the core 161. Instead of twelve filaments 163, it is also possible to provide more (for example 14, 18 or more) or fewer (for example 3, 4, 6 or 10) of said filaments 163. With a higher number, it is also possible for the filaments to be monofilaments. The core 161 here is delimited by an elastically, plastically or geometrically radially extensible membrane and contains no, one or several (here three) stitch threads 164 for taking up strong tensile loads, for example in the event of falls 86. In the core 161, there is also a gel or a matrix 165, in which it is possible to incorporate osmotically active, particulate substances 166, or substances enclosed in vesicles, for example salt crystals. The salt crystals can also be replaced by other osmotically active substances. These inclusions 166 can then take up liquid by osmosis, in the manner described above, and, by expansion of the core, can lead to a shortening and therefore tightening of the thread 160. This shortening is supported by the crosswise arrangement of the sleeve filaments 163, whereas the central stitch threads define the maximum strength of the thread 160 and at the same time limit the compression of the core 161.

FIG. 14 shows a schematic view of a part of a joining element 170 with a thread with tubular core 161 according to an illustrative embodiment of the invention. The thread 170 is composed of a core 161 and of a mesh sleeve 162. The same reference numbers have the same meaning or similar meaning in all of the illustrative embodiments. The core 161 comprises a tubular membrane 177, which can be provided with a coating 171. As has been described in the earlier embodiments, the coating can influence the diffusion properties or also reduce the friction between the core and the shearing filaments, for example, and thus increase the efficiency of the osmotic process, or it can be designed as an axially folded, pleated rigid membrane (in contrast to the smooth elastomeric membrane 177) and limit the swelling process and obstruct swelling of the core out of the braid. Examples of materials for substance transport: PVD coating or CVD coating or polymer coating; for limiting the expansion: stiff structural polymer such as polyamide or polyolefin.

The three stitch threads 164 are surrounded by a saturated salt solution 175 or by another osmotically active substance, in which further particulate salt crystals 176 can be present for taking up further liquid for maintaining the saturated solution. The mesh sleeve 162 with the filaments 163 is designed in the same way as in the previous illustrative embodiment. The liquid can be, for example, an aqueous solution, a hydrophilic liquid (for example higher alcohols, DMSO), or a hygroscopic, biocompatible liquid or a hydrophobic liquid (examples oils). The degree of hydrophobicity of the liquid can be used to influence the speed of diffusion and therefore the kinetics of the osmotic effect. Analogously to the embodiments described in FIG. 7, the stitch threads can also be embedded in a gel-like or elastomeric matrix, in which osmotically active substances in solid or liquid form are incorporated in order to achieve the osmotic swelling. If the matrix is sufficiently stable in itself, for example in the case of an elastomeric matrix, it is also possible to dispense with the membrane 171.

The coating could also be of TPU. Stitch threads, in analogy with what has been described above, can also be omitted, can be present in a different number, or can be applied on the outside of the core.

Figure 15:
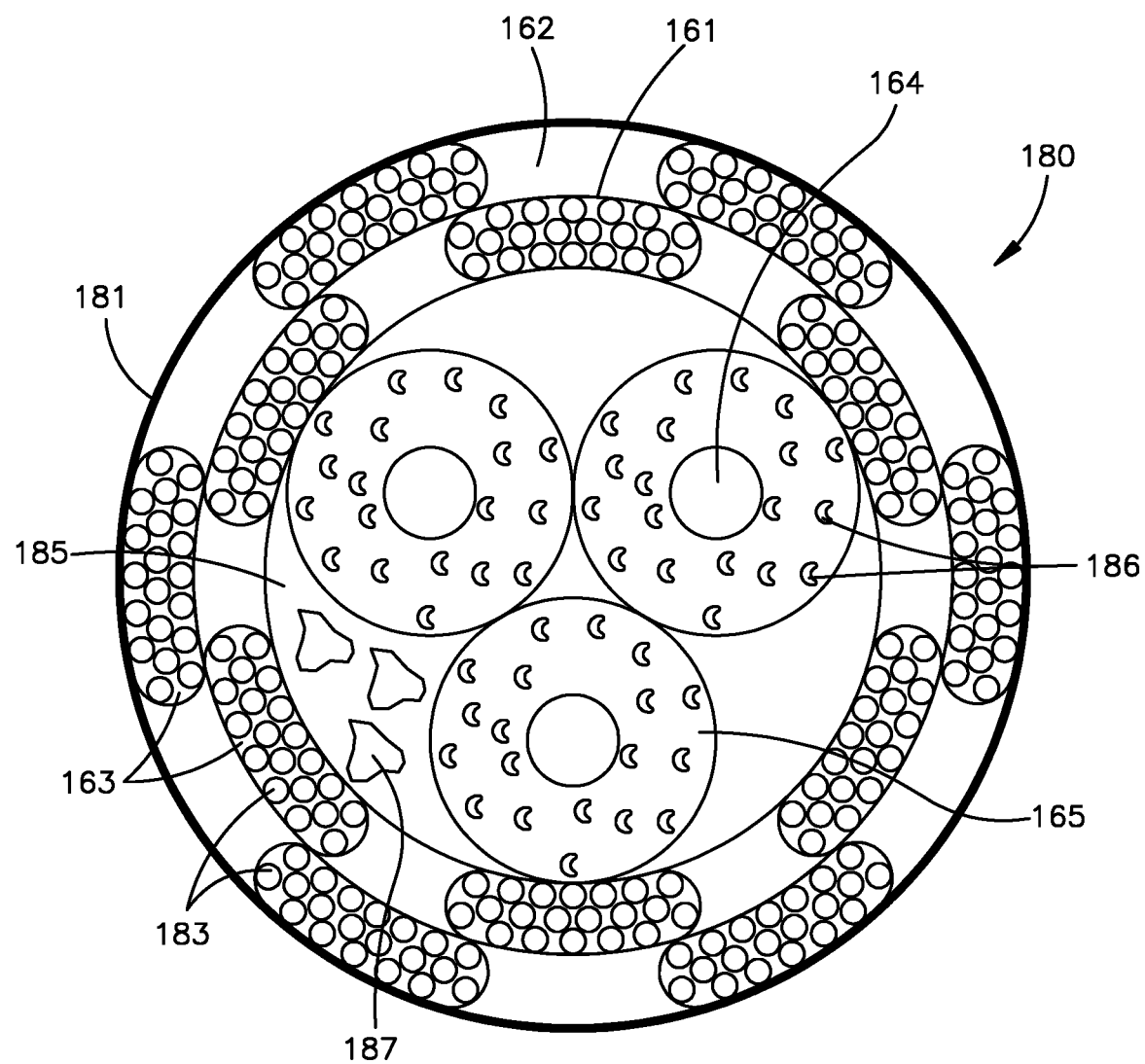
FIG. 15 shows a schematic view of a cross section through a joining element with a multicore thread with an outer membrane according to an illustrative embodiment of the invention.

As a variation to the embodiment shown in FIG. 14, FIGS. 15-17 illustrate different designs of the thread structuring. FIG. 15 shows a schematic cross-sectional view of a joining element 180 with a multicore thread 161 with an outer membrane 181 according to an illustrative embodiment of the invention. Three cores 161 are provided here, which are surrounded by an osmosis membrane and which, for example, each have a gel filling 165 in which salt crystals 186 are embedded. Depending on the strength of the thread that is to be produced, it is also possible to provide four, five, six or more cores 161 which are surrounded for example, but not necessarily, by a membrane on which the filaments 163 of the sleeve 162 are arranged. The (multi)filaments 163 of the sleeve 162 each comprise a multiplicity of individual filaments 183 which are present in the depicted form as a result of the tensile stress that is exerted. The thread 180 as a whole is surrounded by a sleeve 181, which seals the thread off from the outside. In contrast to the threads in FIGS. 13 and 14, the braided filaments 163 here are inside the osmotic chamber. In particular, the space 185 can also be filled by the solution whose concentration decreases as a result of the uptake of liquid. The space 185, and also the spaces enclosed by the membranes 163 and 181, can contain vesicles 187 filled with active substances, or can directly contain active substance solutions 188, which are subjected to pressure by the radial expansion of the core structures and thus expel one or more active substances, which are released through the membrane 181 into the surrounding tissue. As in the other illustrative embodiments, specific features of this illustrative embodiment too can be replaced by other features described here, for example as regards the number and position of stitch threads.

Figure 16:
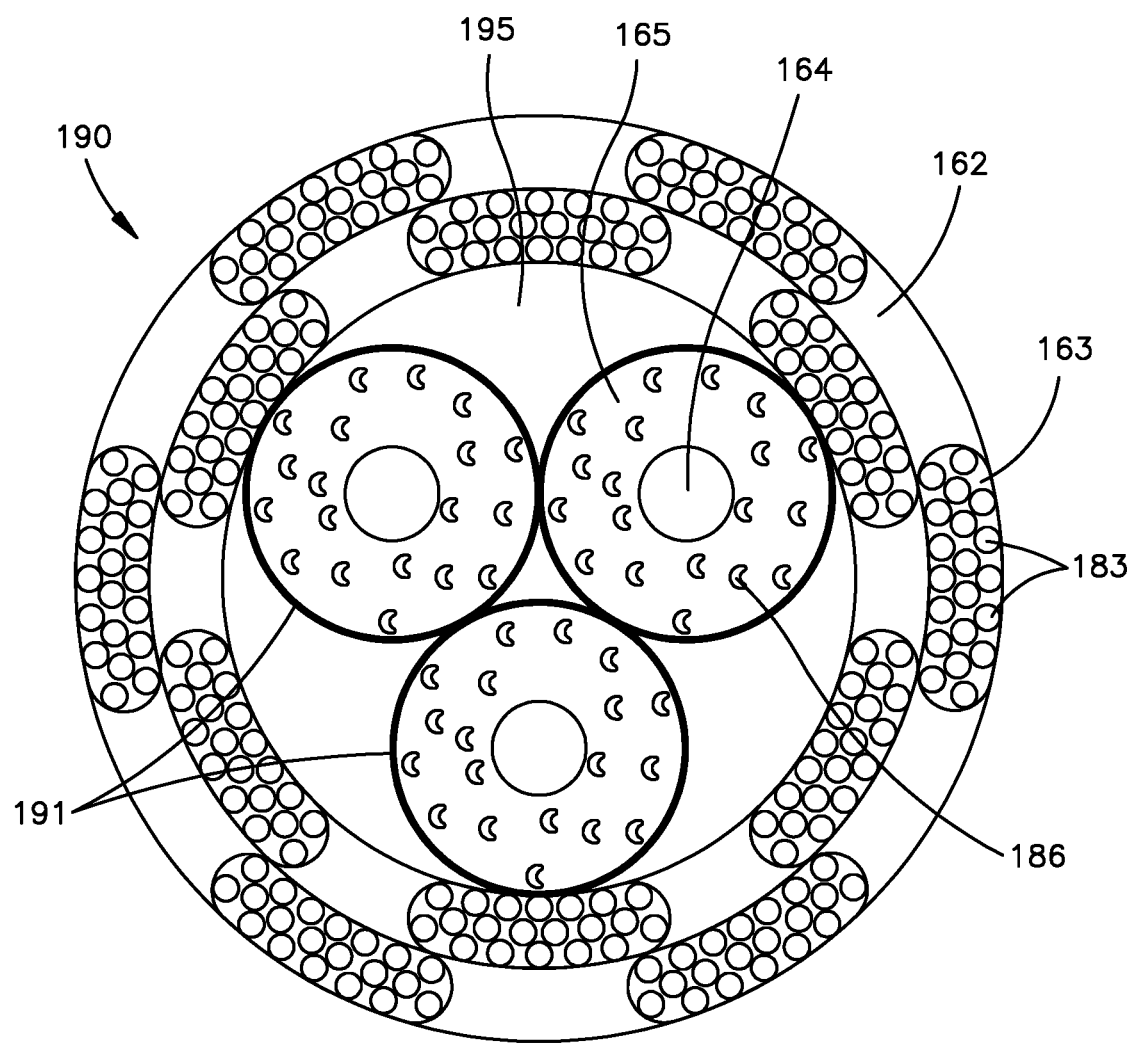
FIG. 16 shows a schematic view of a cross section through a joining element with a multicore thread, with in each case its own membrane according to an illustrative embodiment of the invention.

FIG. 16 shows a cross section through a joining element 190 with a multicore thread 190 with in each case a core membrane 191 according to an illustrative embodiment of the invention. The three cores 164 here are each surrounded by the osmotic liquid or gel or elastomeric polymer 165 with incorporated salt crystals 186, which as a whole, and per core 164, is closed of by an osmotically acting membrane 191 (or in the case of the elastomer also only a core without membrane, otherwise possibly also a core without stitch thread if this structure is inherently stable with or without membrane). The braided mesh sleeve 162 is provided around these closed cores 164, which can be twisted or are advantageously arranged in parallel alongside one another. The space 195 between the core membranes 191 and the inner filaments of the mesh sleeve 162 can be filled initially upon expansion of the membrane 191, before the desired shortening of the thread. An onset time is thus provided in the thread which, referring back to FIG. 12, can lead at the start to a monotonic increase in tension.

Figure 17:
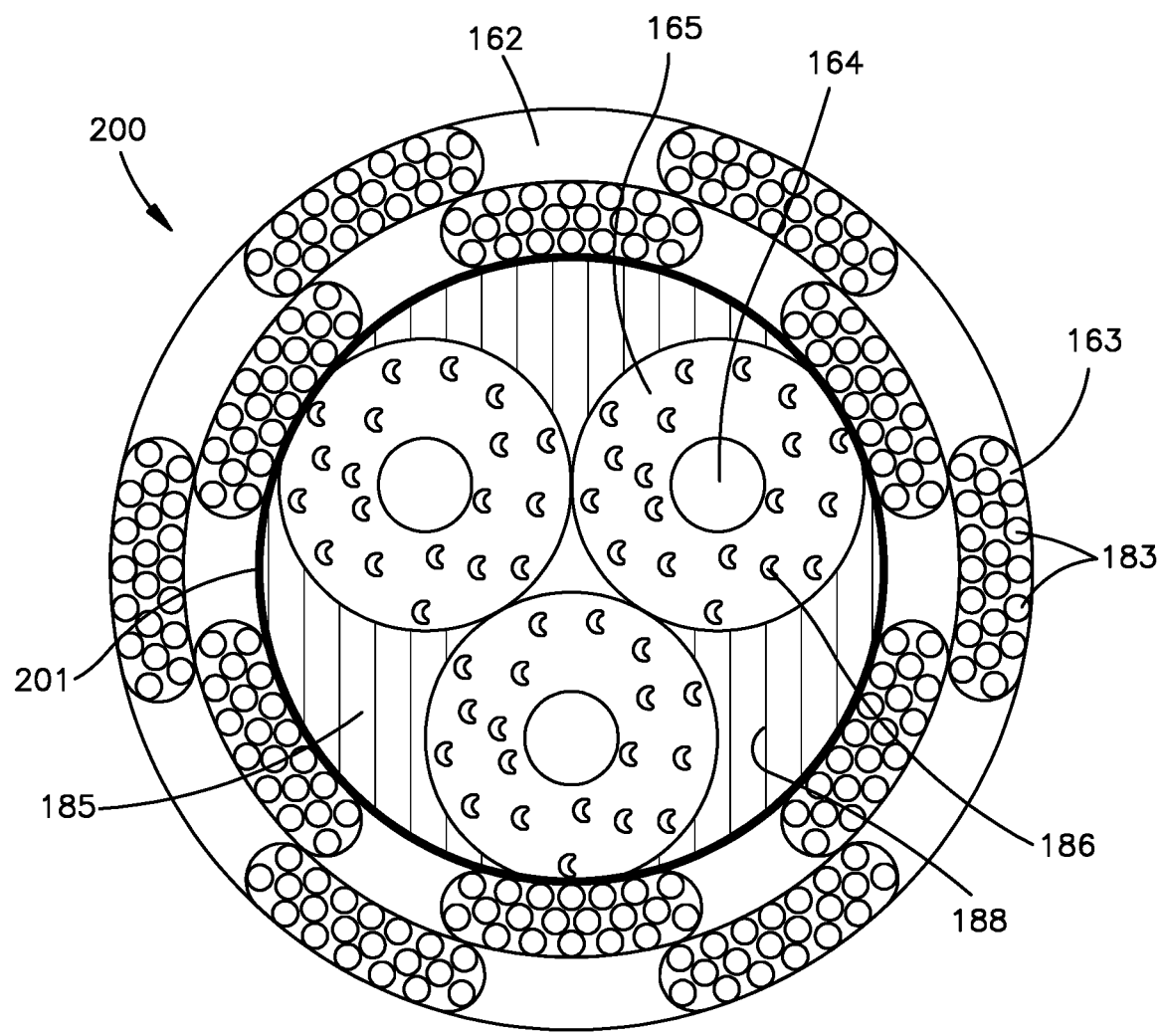
FIG. 17 shows a schematic view of a cross section through a joining element with a multicore thread, with an inner common core membrane, according to an illustrative embodiment of the invention.

FIG. 17 shows a schematic cross-sectional view of a joining element 200 with a multicore thread 164 with an inner common core membrane 201 according to an illustrative embodiment of the invention. This is an embodiment which, in terms of its features, lies between the embodiments in FIG. 15 and FIG. 16. The core membrane 201 here is arranged inside the braided mesh sleeve 162, but instead of surrounding each individual core 164 it surrounds the cores 164 as a whole, such that the space 185 lies within the membrane 201 and can also be used, as is illustrated in FIG. 15, for the inclusion of systems that release active substance. The mesh sleeve 162 then surrounds these.

From these illustrative embodiments, it will be clear that the invention is not intended to be limited to one of these illustrative embodiments. Instead, every combination of these features is also covered by the invention. Thus, the individual threads with the stitch threads 164 can be a liquid, gel-like or polymer substance. However, it could also have no stitch thread as such, but only the matrix; several matrix threads in the core could be of advantage in the case of threads of relatively large calibre, because they make the thread softer, and, in addition, the diffusion kinetics with several small-calibre threads are accelerated compared to those with a large-calibre thread.

The number of stitch threads (here three) can be varied between none and several dozen. The mesh sleeve 162 is here composed of a multifilament 163 with in each case nineteen monofilaments 183. It is clear that both the nature of the multifilaments 163 and also the number of the monofilaments 183 can be varied. The former number can be chosen in particular between three and ten, and the latter number between ten and over one hundred. In the case of a relatively rigid inner membrane, it is possible in some cases to do without a complete covering of the mesh sleeve, since the membrane cannot then protrude between the defects in the cover. It is important to have a membrane sleeve which permits the diffusion but at the same time limits the pressure difference, such that failure of the membrane can be reliably avoided. This purpose is also served by the stitch threads 164, which take up sudden tensile loads and reliably avoid excessive compression of the core of the thread in the event of falls. It is thus clear to a person skilled in the art that features of all the illustrative embodiments described can be combined directly with one another and interchanged.

Figure 18:
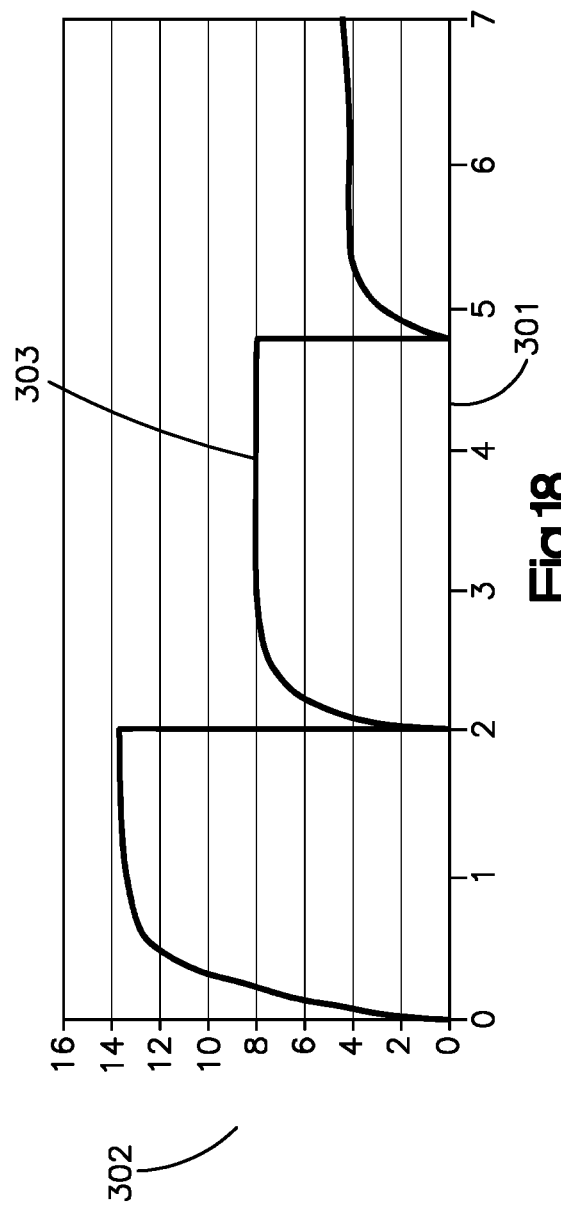
FIG. 18 shows an experimentally measured curve in which the force taken up by the thread is plotted against time.

A number of tests have been carried out using suitably prepared threads and are set out as examples of possible illustrative embodiments. Thus, the curve in FIG. 12 has been verified by a test involving lifting of a weight. This is shown in FIG. 18 by a curve 303 in which the lifted force 302 is plotted against time 301. The tested thread is a thread according to FIG. 13 (but without stitch threads 164 and membrane 161) with a weight ratio of silicone matrix to salt of 1:1, where the particle size of the crystals 166 is smaller than 70 micrometers and where the thread is securely fixed in distilled water at a temperature of 37 degrees Celsius. The thread tension is measured continuously. The tensile force (thread tension) increases in less than one day to over 12 newtons, in order then to move to a state of equilibrium limited by the sleeve. The thread has become deliberately loose after two days, which corresponds for example to a fall by the patient with a ligament sutured by such a thread. The loosening can be achieved simply by a lengthening. The thread tension build-up thus begins anew, but this time to a lesser extent, the built-up spring tension only reaching a tensile force of ca. 8 newtons. The state of equilibrium was maintained here for just under three days in order to carry out a renewed loosening. In this third area, after 5 days and more, tension can be built up over 4 newtons, the flat curve 303 now showing that the maximal tension in the thread has been built up.

Figure 19:
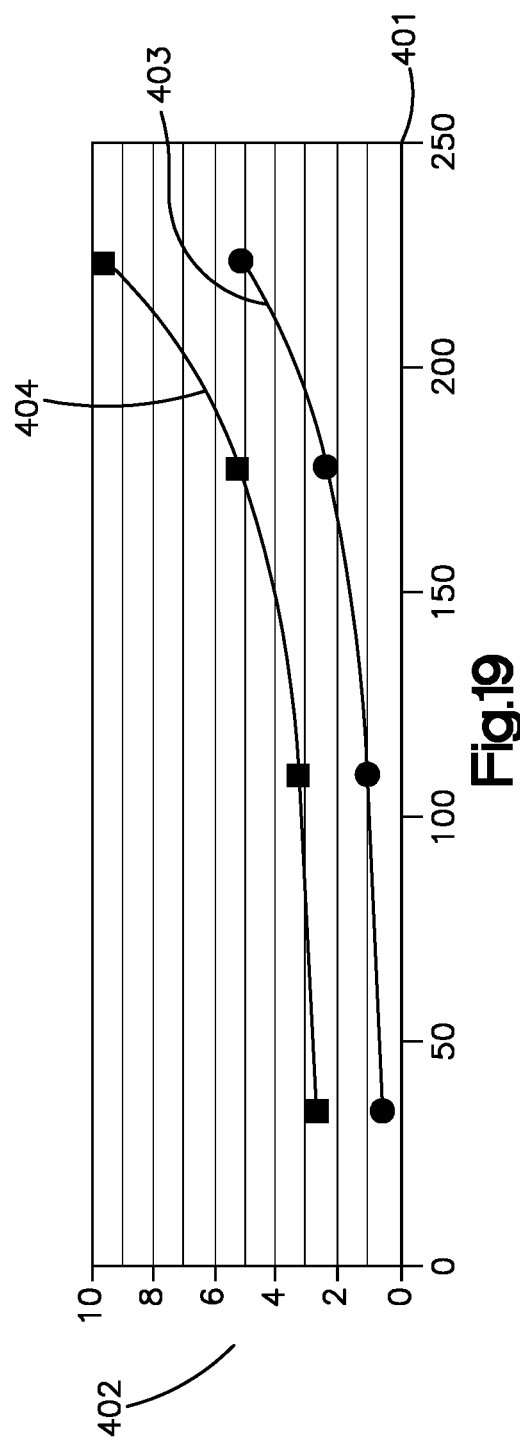
FIG. 19 shows two experimentally measured curves in which the shortening obtained through the contracting thread is plotted against the granulation for different silicone/salt ratios.

FIG. 19 shows a schematic view of two curves 403 and 404, in which the time until the maximum shortening 402 has occurred through the shortening thread is plotted against the granulation 401 for different silicone/salt ratios. FIG. 18 had a silicone/salt ratio of 1:1. This means that the filling 165 has been to crystals 166 in a ratio by weight of 1:1. The two curves 403 and 404 show the duration up to the maximum shortening as function of the granulation 401 of the salt crystals, this duration being shorter at a ratio of 2:1 silicone to salt than at a ratio of 0.71:1, that is to say if more salt is contained in the core. It should be noted that these are not general rules but experimental results, the characteristics of which can change significantly as a function of further parameters, for example the local distribution of the salt crystals, the agglomerate formation and the structure of the polymer. In the small granulation range of below 50 to ca. 150 micrometers, hardly any differences arise, whereas at greater granulation the duration until the maximum shortening increases rapidly.

Figure 20:
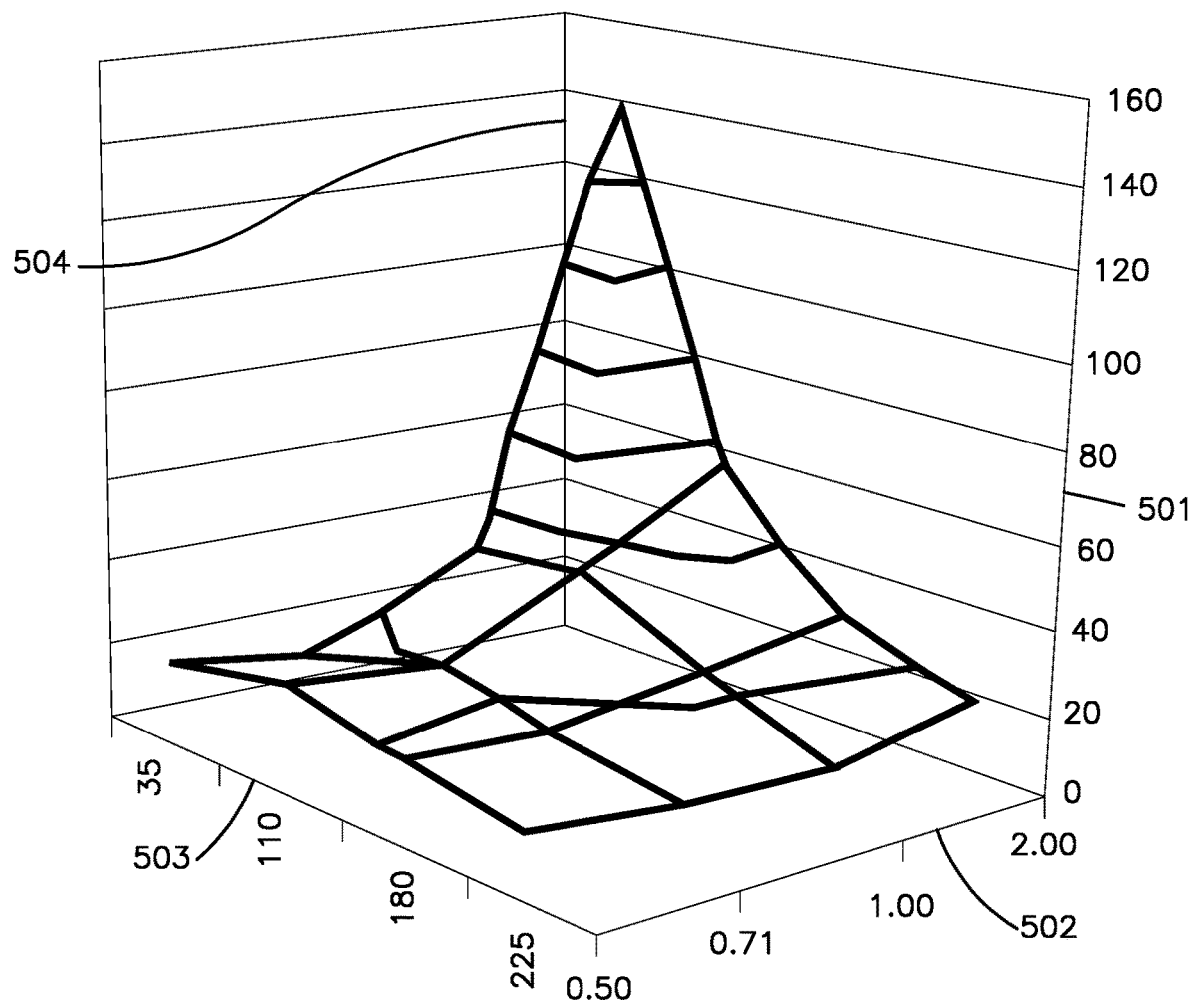
FIG. 20 shows an overview of the experimentally determined ratios between initial shortening (in percent per day), compared to the weight ratio of silicone to salt for granulation (in micrometers)

The three-dimensional curve 504 in FIG. 20 provides an overview of the ratios between initial shortening 501 (in percent per day) relative to the ratio by weight of silicone to salt 502 for the granulation 503 (in micrometers). A lot of silicone relative to the salt and small granulations provide a rapid shortening in time, whereas both large granulations and also a higher salt content lead to a smaller shortening per day. By suitable choice of the individual components, a person skilled in the art can therefore define the behavior of the thread to a large extent.

The following should be noted in particular. Joining elements in the form of a thread can be produced in diameters of as little as 50 micrometers (and less), if it is surgical applications that are concerned. For thicker threads, a twisted or drilled structure can be formed, generally expressed as a multifilament structure. The advantage of these is that, in the joining elements thus produced, the rubbing of the individual threads affords greater strength, while on the other hand, for the same reason, the large number of twisted or drilled threads provides a reduced stiffness.

In a thread of 50 micrometers diameter, it is expedient to use powders of the salt crystals of less than 100 nanometers to 1 micrometer.

From each of these crystals, small centers of osmotic activity are formed. In particular, these centers, which involve vesicles formed around such salt cores, should be smaller by a factor of approximately 10 than the diameter of the swelling core. A small number of centers provides a more reliable osmotic activity than with a few large crystals. The speed of the shortening of such threads, corresponding to the teaching of their construction, is advantageously set by the properties of the polymer material used for the swelling core.

Figure 21:
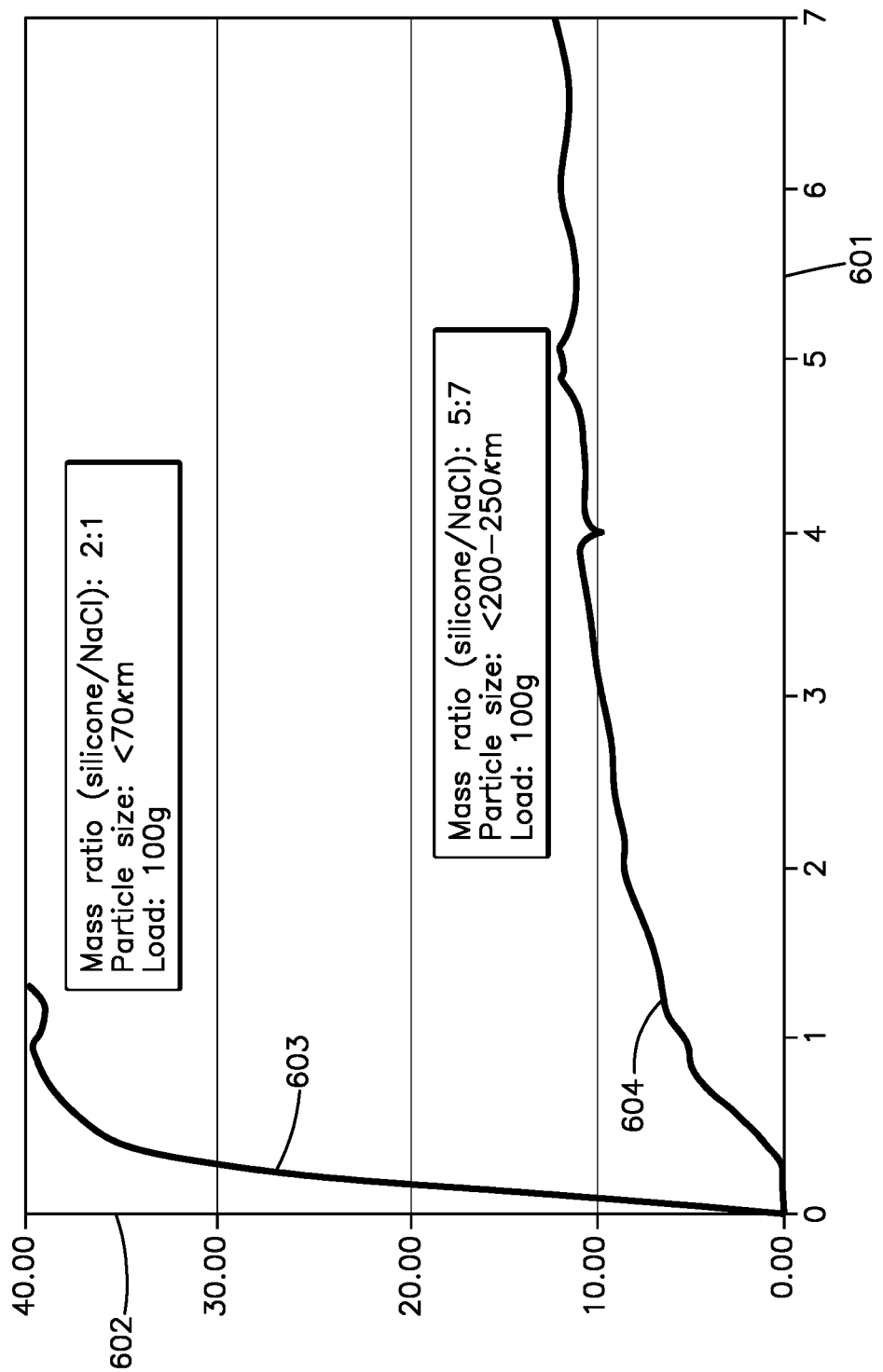
FIG. 21 shows two experimentally determined curves in which the shortening obtained through the contracting thread is plotted in percent against time for different silicone/NaCl ratios.
Figure 22:
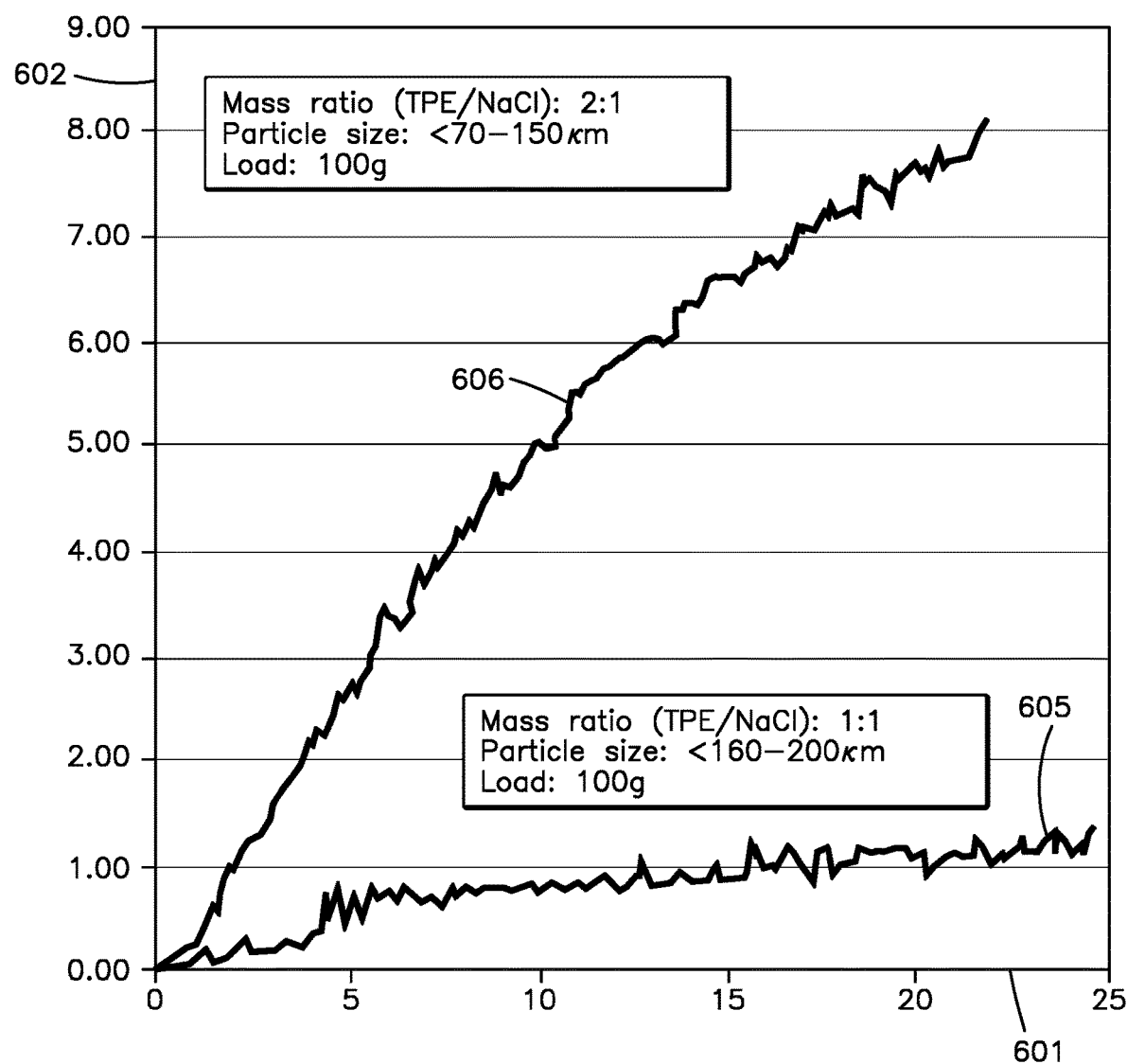
FIG. 22 shows two experimentally determined curves in which the shortening obtained through the contracting thread is plotted in percent against time for different TPE/NaCl ratios.

FIGS. 21 and 22 each show a view of two measured curves, in which the shortening 602 afforded by the contracting thread is plotted in percent against time 601 for different silicone/NaCl (salt) ratios 603/604 and for different TPE/NaCl (salt) ratios 605/606.

It will be noted that, in a silicone thread with a mass ratio of silicone to NaCl of 2:1 at an average particle size of the salt crystals of less than 70 micrometers and a constant thread tension of 1 newton, a state of equilibrium of the curve 603 is obtained after about one day at high shortening level. By contrast, a four-times smaller shortening is seen at a mass ratio of silicone to NaCl of 5:7 at an average particle size of the salt crystals of less than 200 to 250 micrometers and a substantially constant thread tension of 1 newton in the curve 604, which is achieved after about 4 days. The core had a diameter of 0.7 millimeter.

The tests with TPE threads were carried out in another time horizon. It will be noted that, in a TPE thread with a mass ratio of TPE to NaCl of 1:1 at an average particle size of the salt crystals of less than 160 to 200 micrometers and a constant thread tension of 1 newton (that is to say as in the other test), a state of equilibrium of the curve 605 after ca. twenty to twenty-five days is obtained at a very small shortening level of one percent. By contrast, an eight-times greater shortening can be seen at a mass ratio of TPE to NaCl of 2:1 at an average particle size of the salt crystals of less than 70 to 150 micrometers and a similarly constant thread tension of 1 newton in the curve 604, which even after more than twenty days has not yet reached a state of equilibrium.

It is thus evident to a person skilled in the art that, when using TPE and silicone thread cores with different salt content and granulation, a suitable shortening can be set between 40 percent in one day and one percent in five days, which corresponds to a difference in the speed by a factor 200. These values can additionally be modulated by suitable use of membranes (more or less permeable; more or less flexible in extension). The results presented here with threads having a core can accordingly be transposed to the other illustrative embodiments.

In addition to silicone, which can be used in different qualities, this applies to an even greater extent for threads with TPE filling, that is to say for thermoplastic threads. These thermoplastic elastomers can be very easily shaped, because they pass through the plastic state during processing. They can be produced in particular in hardnesses of 5

Shore A to 90 Shore D. Their flowability and their density and other properties can be adjusted by compounding with a wide variety of fillers and additives. TPE-V has good rubber-like properties, for example ethylene/propylene terpolymer/propylene, crosslinked or natural rubber/polypropylene.

The second material thus comprises a swelling material, in particular a hygroscopic material, such as NaCl, which has the advantage of easily establishing a state of equilibrium in the body, without placing too great a strain on the patient's body as a result of the osmotic activity. The swelling of the second material is achieved by osmosis, that is to say by diffusion of water from the space containing liquid surrounding the joining element (in vitro, for example, water or physiological saline solution in a beaker; and in vivo by the body fluids surrounding the implant site of a thread) through a semipermeable or selectively permeable membrane, which the person skilled in the art chooses as appropriate.

The illustrative embodiments in FIGS. 12 to 22 are in direct relation to the disclosure of FIGS. 1 to 11. The first material can thus be regarded as the stitch thread or stitch threads and/or axial threads in the mesh sleeve and the membrane or axial thread reinforcements in the membrane or membranes. The second material, which slowly contracts over a longer period of time, is the one or more chambers 165, 185 in which the crystals contributing to the swelling are incorporated. A shearing of the first material surrounding the second material is afforded in particular by provision of braided mesh sleeve. The slow contraction of the second material over a second period of time longer than the first period of time is understood also as the combination of the effect with the first material, as arises with the braided thread. The important factor is simply that, for in each case two corresponding local reference points in the element, the distance shortens over a period of time, in other words a tension builds up between these two points. If these points are not firmly fixed, the distance between them shortens, which corresponds to a contraction of the second material.

It is also possible, however, for the membrane itself to be welded together at short axial distances of 3 to 10 times the length of the normal diameter of a thread at suture points, in order to produce individual axially defined chambers, which shorten in length upon swelling. To this extent, all uses for the disclosed prosthetic material are also covered for joining elements designed according to the teaching of FIGS. 12 to 22.

During the shorter-lasting load, a cramping or a spasm can also build up the tissue dislocation, a peak load and a slightly slower build-up.

LIST OF REFERENCE NUMBERS 10 part of a joining element
11 core
12 jacket (originally)
13 joining construction (mesh)
14 knot
15 arrow
16 jacket (deformed)
20 part of a joining element
22 jacket (originally)
26 jacket (deformed, in degradation)
30 joining element
31 molecule
33 direction of release
34 arrow
40 joining element
11 core
42 jacket (originally)
43 mesh
44 angle (to begin with)
45 angle (later)
46 mesh
47 salt crystals
48 vesicles charged with active substance
49 active substances
50 joining element
51 base material
52 thread molecules (to begin with)
53 thread molecules (later)
61 resulting change in diameter
62 resulting change in length
63 resulting change in volume
64 thread angle range
65 resulting change in force
71 time
72 thread tension
73 change-over taut ⇔ loose
74 conventional thread
75 relaxation
76 fall
77 further relaxation
84 thread according to the invention
85 tightening
86 fall
87 further tightening
160 thread
161 core
162 mesh envelope
163 envelope filaments
164 stitch threads
165 matrix
166 salt crystal
170 thread
171 coating
175 salt solution
176 salt crystals
177 tube membrane
180 thread
181 outer membrane
183 monofilament
185 space with osmotic liquid
186 salt crystals
187 vesicles with active substance
188 active substance solutions
190 thread
191 core membrane
195 space between cores and envelope
200 thread
201 multicore membrane
301 time
302 force lifted
303 curve
401 granulation
402 shortening
403 curve for high salt content in silicone
404 curve for low salt content in silicone
501 initial shortening 501 (in percent per day)
502 ratio by weight of silicone to salt
503 granulation (in micrometers)
504 three-dimensional curve
601 time (in days)
602 shortening (in percent)
603-606 curves for different threads

What is claimed:

1. A joining element elongate along a longitudinal direction, the joining element comprising:
   a core that extends substantially along the longitudinal direction, the core comprising a polymer material and an osmotically active substance distributed in the polymer material; and
   a sleeve surrounding at least a portion of the core along the longitudinal direction and defining a length in the longitudinal direction between opposed ends of the sleeve, the sleeve comprising at least one thread, wherein the at least one thread defines an angle of intersection with respect to the longitudinal direction,
   wherein the osmotically active substance has a variable distribution density through the polymer material, and the variable distribution density varies radially with respect to the longitudinal direction.

2. The joining element of claim 1, wherein the polymer material comprises an elastomer.

3. The joining element of claim 2, wherein the elastomer comprises a thermoplastic elastomer or a cross-linked elastomer.

4. The joining element according to claim 2, wherein the elastomer comprises silicone and the osmotically active substance comprises salt crystals.

5. The joining element according to claim 2, wherein the core is extruded.

6. The joining element of claim 2, further comprising a diffusion-limiting membrane surrounding the core, wherein the membrane is an elastomer membrane.

7. The joining element of claim 1, wherein the core is configured for controlled release of the osmotically active substance.

8. The joining element of claim 1, wherein the sleeve is configured to slide along the core upon a fluid expansion of the core such that the angle of intersection increases.

9. The joining element of claim 1, wherein the osmotically active substance is disposed in a vesicle within the core.

10. The joining element of claim 1, wherein the osmotically active substance is dissolved within the polymer material.

* * * * *